(12) United States Patent
Lauermann

(10) Patent No.: US 6,635,472 B1
(45) Date of Patent: Oct. 21, 2003

(54) RETROVIRUS AND VIRAL VECTORS

(75) Inventor: Vit Lauermann, Baltimore, MD (US)

(73) Assignee: Rubicon Laboratory, Inc., Baltimore, MD (US)

( * ) Notice: Subject to any disclaimer, the term of this patent is extended or adjusted under 35 U.S.C. 154(b) by 0 days.

(21) Appl. No.: 09/134,360

(22) Filed: Aug. 14, 1998

Related U.S. Application Data

(60) Provisional application No. 60/055,864, filed on Aug. 15, 1997, and provisional application No. 60/091,734, filed on Jul. 6, 1998.

(51) Int. Cl.$^7$ .................. C12N 15/79; C12N 15/83; C12N 15/867; C12N 15/85; A61K 39/21

(52) U.S. Cl. .............. 435/320.1; 435/69.1; 435/171.1; 435/172.3; 435/240.1; 435/240.2; 536/23.1; 536/23.5; 536/24.1; 536/23.72; 424/185.1; 424/188.1; 424/192.1; 424/199.1; 424/204.1; 424/205.1; 424/230.1; 424/231.1; 424/232.1; 424/233.1

(58) Field of Search .................. 435/69.1, 320.1, 435/171.1, 172.3, 240.1, 240.2; 424/185.1, 188.1, 192.1, 199.1, 204.1, 205.1, 230.1, 231.1, 232.1, 233.1; 536/23.72, 23.1, 23.5, 24.1

(56) References Cited

U.S. PATENT DOCUMENTS 5,624,820 A * 4/1997 Cooper et al. .............. 435/69.1

OTHER PUBLICATIONS

Kinsella et al Hum. Gene Ther. 1996, vol. 7, pp. 1405–1413.*
Cannon et al. J. Virol. 1996, vol. 70, pp. 651–657.*
Verma et al. Nature 1997, vol. 389, pp. 239–242.*
Usmani et al. RNA virus 2000, pp. 252–2257.*
Orkin et al. 1996 Report and Recommendations of the Panel to Assess the NIH Investment in Research on Gene Therapy.*
Weatherall D.J. British Medical Bulletin 1995, vol. 1, pp. 1–11.*
Smith A.E. The Lancet 1999, vol. 354 suppli 1. pp. 1–4.*
The Journal of Experimental Medicine, vol. 178, Aug. 1993, pp. 461–468, "Autoimmune Disease in Mice Due to Integration of an Endogenous Retrovirus in an Apoptosis Gene" by J. Wu et al.
Journal of Virology, Jan. 1996, pp. 651–657, "Conserved Sequences in the Carboxyl Terminus of Integrase that are Essential for Human Immunodeficiency Virus Type 1 Replication" by P.M. Cannon et al.
Journal of Virology, May 1995, pp. 3216–3219, "Integration Is Required for Productive Infection of Monocyte–Derived Macrophages by Human Immunodeficiency Virus Type 1" by G. Englund et al.

Cell, vol. 23, 323–334, Feb. 1981, "Avian Leukosis Virus–Induced Tumors Have Common Proviral Integration Sites and Synthesize Discrete New RNAs: Oncogenesis by Promoter Insertion" by B.G. Neel et al.
Proc. Natl. Acad. Sci. USA, vol. 82, pp. 1054–1058, Feb. 1985 Biochemistry, "Retroposon insertion into the cellular oncogene c–myc in canine transmissible venereal tumor" by N. Katzir et al.
Journal of Virology, Oct. 1992, pp. 6107–6116, "Phenotypes of Murine Leukemia Virus–Induced Tumors: Influence of 3' Viral Coding Sequences" by D. E. Ott et al.
Journal of Virology, Feb. 1996, pp. 721–728, "Human Immunodeficiency Virus Type 1 Integrase Mutants Retain In Vitro Integrase Activity yet Fail To Integrate Viral DNA Efficiently during Infection" by A.D. Leavitt et al.
Proc. Natl. Acad. Sci., vol. 77, No. 5, pp. 2994–2998, May 1980, Microbiology, "Synthesis and circulation of N– and B–tropic retroviral DNA in FV–1 permissive and restrictive mouse cells" by W.K. Yang et al.
Journal of Acquired Immune Deficiency Syndromes, 3:852–858, 1990 Raven Press, Ltd., New York, "Terminal Nucleotides of the Preintegrative Linear Form of HIV–1 DNA Deduced from the Sequence of Circular DNA Junctions" by J. Kulkosky et al.
Fields Virology, Third Edition, Lippincott–Raven Publishers, Philadelphia, PA 1996, "Polyomavirinae: The Viruses and Their Replication" by C. N. Cole.
Fields Virology, Third Edition, Lippincott–Raven Publishers, Philadelphia, PA 1996, "Polyomaviruses" by K. V. Shah.
Journal of Virology, Mar. 1993, pp. 1169–1174, "Integration is Essential for Efficient Gene Expression of Human Immunodeficiency Virus Type 1" by H. Sakai et al.
Virology 179, 886–889, 1990, Two Bases Are Deleted from the Termini of HIV–1 Linear DNA During Integrative Recombination: by C. D. Pauza.
Journal of Virology, Oct. 1990, pp. 4903–4906, "Sequence of the Circle Junction of Human Immunodeficiency Virus Type 1: Implications for Reverse Transcription and Integration" by J.M. Whitcomb et al.

(List continued on next page.)

*Primary Examiner*—James Housel
*Assistant Examiner*—Bao Qun Li

(57) ABSTRACT

This invention relates to the fields of genetic engineering, virus replication and gene transfer. More specifically, this invention relates to polynucleotide construct, recombinant virus, transposon, and their vectors, wherein an ori derived from a DNA virus capable of replicating in vertebrate cells is inserted into the retrovirus, allowing the retrovirus following the reverse transcription to efficiently replicate as extrachromosomal or episomal DNA without the necessity of integration into the host cell chromosome. Additionally, this invention relates to polynucleotide construct, recombinant virus, transposon, and their vectors replicating episomally without aid of an ori and related elements. Also, this invention encompasses preventive, therapeutic, and diagnostic applications employing said constructs, viruses and vectors.

24 Claims, 9 Drawing Sheets

OTHER PUBLICATIONS

Journal of Virology, Dec. 1990, pp. 6286–6290, "Analysis of Long Terminal Repeat Circle Junctions of Human Immunodeficiency Virus Type 1" by J.S. Smith et al.

Journal of Virology, Jan. 1991, pp. 551–555, "Circular DNA of Human Immunodeficiency Virus: Analysis of Circle Junction Nucleotide Sequences" by T. Hong et al.

Journal of Virology, May 1990, pp. 2421–2425, "Integration Is Not Necessary for Expression of Human Immunodeficiency Virus Type 1 Protein Products" by M. Stevenson et al.

Journal of Virology, Jul. 1991, pp. 3906–3910, "The Sequence of Human Immunodeficiency Virus Type 2 Circle Junction Suggests That Integration Protein Cleaves the Ends of Linear DNA Asymmetrically" by J. M. Whitcomb et al.

Virology 191, 72–80, 1992, "Evidence of Human Polyomavirus BK and JC Infection in Normal Brain Tissue" by C. Elsner et al.

Nature Medicine, vol. 4, No. 7, Jul. 1998, "All in the p53 family" by K. Novak

Cell, vol. 42, pp. 573–580, Sep. 1985, "Mutants and Pseudorevertants of Moloney Murine Leukemia Virus with Alterations at the Integration Site" by J. Colicelli et al.

Proc. Natl. Acad. Sci., vol. 81, pp. 4149–4153, Jul. 1984, "Construction of mutants of Moloney murine leukemia virus by suppressor–linker insertional mutagenesis: Positions of viable insertion mutations" by L. I. Lobel et al.

Journal of Virology, Oct. 1990, pp. 4709–4717, "Analysis of Mutations in the Integration Function of Moloney Murine Leukemia Virus: Effects on DNA Binding and Cutting" by M. J. Roth et al.

Journal of Virology, Aug. 1992, pp. 5092–5095, "A Mutation at One End of Moloney Murine Leukemia Virus DNA Blocks Cleavage of Both Ends by the Viral Integrasae In Vivo" by J.E. Murphy et al.

Journal of Virology, Sep. 1995, pp. 5904–5907, "Sequences in the Human Immunodeficiency Virus Type 1 U3 Region Required for In Vivo and In Vitro Integration" by A. S. Reicin et al.

Journal of Virology, Feb. 1990, pp. 757–766, "Sequence Analysis of Amphotropic and 10A1 Murine Leukemia Viruses: Close Relationship to Mink Cell Focus–Inducing Viruses" by D. Ott et al.

Reverse Transcriptase, Copyright 1993 Cold Spring Harbor Laboratory Press, "Strong–stop Strand Transfer during Reverse Transcription" by A. Telesnitsky et al.

Cell, vol. 23, pp. 175–182, Jan. 1981, "SV40–Transformed Simian Cells Support the Replication of Early SV40 Mutants" by Y. Gluzman.

Journal of Virology, Nov. 1991, pp. 5944–5951, "Regulated Replication of a Episomal Simian Virus 40 Origin Plasmid in COS7 Cells" by T. Chittenden et al.

J. gen Virol. (1977), 36, 59–74, Characteristics of a Human Cell Line Transformed by DNA from Human Adenovirus Type 5' by F. L. Graham et al.

Proc. Natl. Acad. Sci., vol. 90, pp. 8392–8396, Sep. 1993, "Production of high–titer helper–free retroviruses by transient transfection" by W. S. Pear, et al.

Journal of Virology, Jan. 1995, pp. 376–386, "Human Immunodeficiency Virus Type 1 Integrase: Effects of Mutations on Viral Ability to Integrate, Direct Viral Gene Expression from Unintegrated Viral DNA Templates, and Sustain Viral Propagation in Primary Cells" by M. Wiskerchen et al.

Journal of Virology, Jun. 1996, pp. 3922–3929, "Gene Transfer into Mammalian Cells by a Rous Sarcoma Virus––Based Retroviral Vector with the Host Range of the Amphotropic Murine Leukemia Virus" by E. V. Barsov et al.

Journal of Molecular and Applied Genetics, pp. 327–341, 1982, Raven Press, New York, "Transformation of Mammalian Cells to Antibiotic Resistance with a Bacterial Gene Under Control fo the SV40 early Region Promoter", by P.J. Southern et al.

Virology 198, pp. 59–70 (1994), "Infection of Human Polyomaviruses JC and BK in Peripheral Blood Leukocytes from Immunocompetent Individuals", by K. Dörries et al.

Proc. Natl. Acad. Sci. USA, vol. 92, pp. 1292–1296, Feb. 1995, developmental Biology, "Maintenance of an extrachromosomal plasmid vector in mouse embryonic stem cells", by M. Gassmann et al.

Proc. Natl. Acad. Sci. USA, vol. 91, pp. 9233–9237, Sep. 1994, Biochemistry, "Tethering human immunodeficiency virus 1 integrase to a DNA site directs integration to nearby sequences", by F. D. Bushman.

Proc. Natl. Acad. Sci. USA, vol. 95, pp. 4338–4343, Apr. 1998, Cell Biology, "Segregation of viral plasmids depends on tethering to chromosomes and is regulated by phosphorylation", by C. W. Lehman et al.

The EMBO Journal, vol. 15, No. 1 pp. 1–11, 1996, "Cis and Trans requirements for stable episomal maintenance of the VPV–1 replicator", by M. Piirsoo et al.

Journal of Virology, Jan. 1990, pp. 431–436, 1990, American Society for Microbiology, "Protection from Herpes Simplex Virus type 1 Lethal and Latent Infections by Secreted Recombinant Glycoprotein B Constitutively Expressed in Human Cells with a BK Virus Episomal Vector", by R. Manservigi et al.

1996 Rapid Science Publishers, Current Opinion in Oncology 1996, 8:499–508, "Current progress in the gene therapy of cancer" by B. M. Davis et al.

Arch Virol (1995) 140; 335–339, "A BK virus episomal vector for constitutive high expression of exogenous cDNAs in human cells" by S. Sabbioni et al.

* cited by examiner

Figure 1
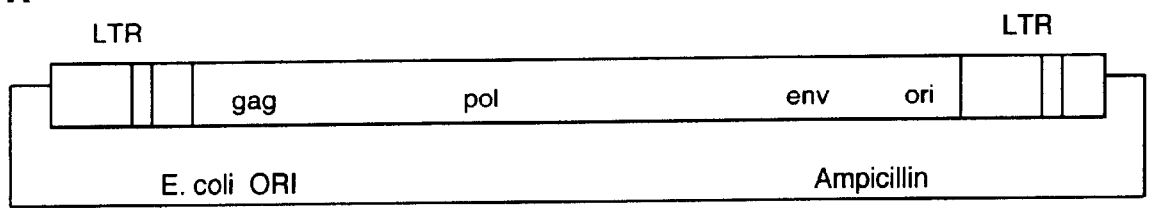
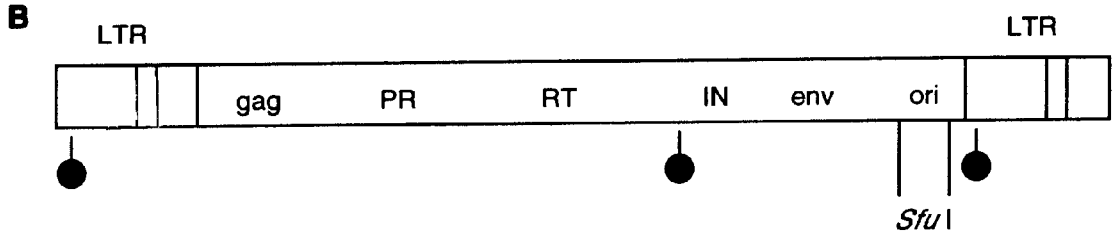
C
```
           LTR >
wild-type  TGAAAGACCCCACC...
IR mutant  TGTATGTCGCGACC...
```
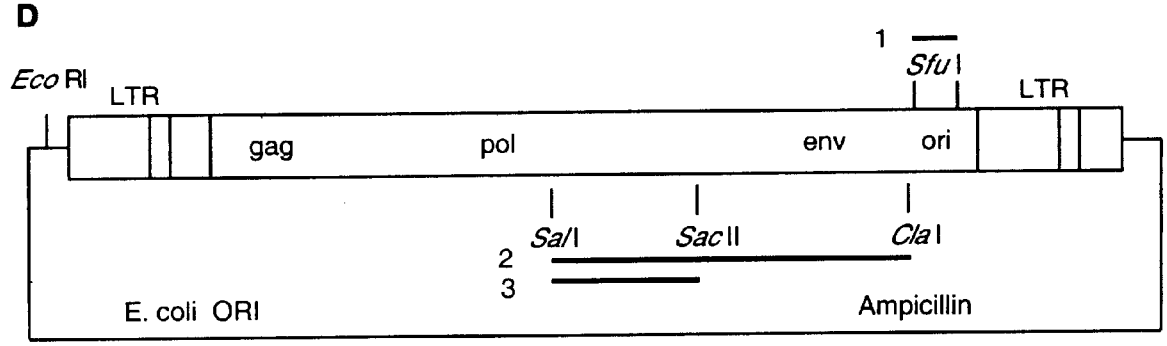

Figure 3
Transfection
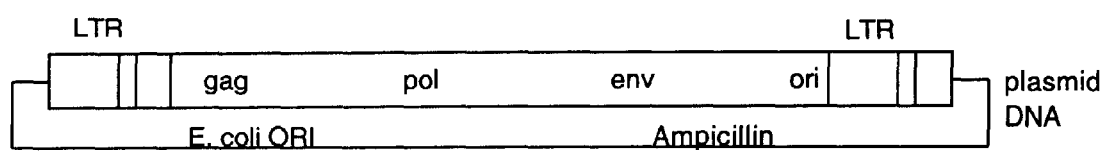
RNA transcription
———————————————————————————— RNA
Infection
Reverse transcription
Transport into the nucleus
DNA circularization
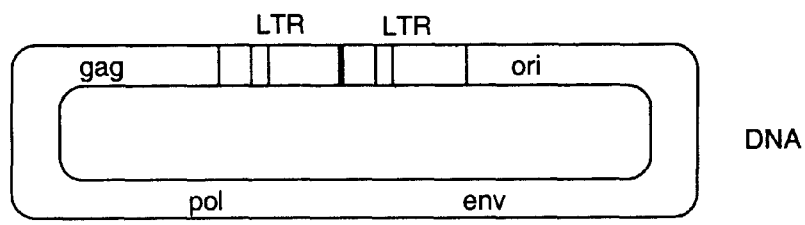
DNA amplification

Figure 6

```
         U5                                                          U3
WT   TGACTACCCGTCAGCGGGGTCTTTCATT                    AATGAAAGACCCCACCTGTAGTTTGGCAAG_CTAGCTTAA
SMC  TGACTACCCGTCAGCGGGGTCTTTCATT                    AATGTATGTCGCGACCTGTAGGTTTGGCAAGGCTAGCTTAA
1    TGACTACCCGTCAGCGGGGTCTTTCAT  ACCTCCA            AATGTATGTCACGACCTGTAAGTTTGGCAAGGCTAGCTTAA
2    TGACTACCCGTCAGCGGGGTCTTTCATT GTATGTCGCA         AATGTATGTCGCGACCTGTAGGTTTGGCAAGGCTAGCTTAA
3    TGACTACCCGTCAGCGGGGTCTTTCAT  ACCTCCA            AATGTATGTCACGACCTGTAGGTTTGGCAAGGCTAGCTTAA
4    TGACTACCCGTCAGCGGGGTCTTTCATT                    AATGTATGTCACGACCTGTACGTTTGGTAAGGCTAGCTTAA
5    TGACTACCCGTCAGCGGGGTCTTTCATT                     ATGTATGTCACGACCTGTAGGTTTGGCAAGGCTAGCTTAA
6    TGACTACCCGTCAGCGGGGTCTTTCATT GG                 AATGTATGTCGCGACCTGTAGGTTTGGCAAGGCTAGCTTAA
7    TGACTACCCGTCAGCGGGGTCTTTCATT                    AATGTATGTCGCGACCTGTAGGTTTGGCAAGGCTAACTTAA
8    TGACTACCCGTCAGCGGGGTCTTTCATT                    AATGTATGTCGCGACCTGTAGGTTTGGCAAGGCTAGCTTAA
9    TGACTACCCGTCAGCGGGGTCTTTCATT                     CGCGACCTGTAGGTTTGGCAAGGCTAGCTTAA
10   TGACTACCCGTCAGCGGGGTCTTTCATT TTT                AATGTATGTCGCGACCTGTAGGTTTGGCAAGGCTAGCTTAA
11   TGACTACCCGTCAGCGGGGTCTTTCATT CGAG               AATGTATGTCGCGACCTGTAGGTTTGGCAAGGCTAGCTTAA
12   TGACTACCCGTCAGCGGGGTCTTTCATT                    AATGTATGTCGCGACCTGTAGGTTTGGCAAGGCTAGCTTAA
13   TGACTACCCGTCAGCGGGGTCTTTCATT                     ATGTATGTCGCGACCTGTAGGTTTGGCAAGGCTAGCTTAA
14   TGACTACCCGTCAGCGGGGTCTTTCATT ACCC               AATGTATGTCGCGACCTGTAGGTTTGGCAAGGCTAGCTTAA
15   TGACTACCCGTCAGCGGGGTCTTTCATT ACCA               AATGTATGTCGCGACCTGTAGGTTTGGCAAGGCTAGCTTAA
16   TGACTACCCGTCAGCGGGGTCTTTCATT                    TGGATGTCGCGACCTGTAGGTTTGGCAAGGCTAGCTTAA
17   TGACTACCCGTCAGCGGGGTCTTTCATT A                  AATGTATGTCCCGACCGGTAGGTTTGGCAAGGCTAACTTAA
18   TGACTACCCGTCAGCGGGGTCTTTCA                      AATGTATGTCGCGACCTGTAGGTTTGGCAAGGCTAGCTTAA
19   TGACTACCCGTCAGCGGGGTCTTTCATT CT                 AATGTATGTCGCGACCTGTAGGTTTGGCAAGGCTAACTTAA
MS   TGACTACCCGTCAGCGGGGTCTTTCATT AANATT             NTGTNTGTANCNANNNGTNGGNNNCGGAAAGCTAACTTAA
```

RETROVIRUS AND VIRAL VECTORS

RELATED APPLICATIONS AND U.S. GOVERNMENT RIGHTS

This application claims priority from U.S. Provisional Patent Application No. 60/055,864 filed Aug. 15, 1997 and U.S. Provisional Application No. 60/091,734 filed Jul. 6, 1998, both of which are incorporated herein by reference. A portion of this invention was supported by a grant from the Federal Government of the United States. The United States of America may have certain rights in the invention.

FIELD OF INVENTION

This invention relates to the fields of genetic engineering, virus replication, and gene transfer.

DESCRIPTION OF RELATED ART

Retroviruses and retroviral vectors are potentially powerful tools for the transfer of genes into animals and humans, for the creation of transgenic animals, and for vaccines. However, the use of the retroviruses has certain disadvantages. Most vexatious of them is the obligatory integration of the DNA form of the viral genome for its expression and replication (Cannon et al., 1996; Englund et al., 1995). The integration may have unforeseen and undesired consequences. It could lead to the transcriptional activation through the juxtaposition of the retroviral promoter/enhancer. It could also result in insertional mutagenesis. Both events could result in the production of tumors (Katzir et al., 1985; Neel et al., 1981; Ott et al., 1992), the former by activation of a dominant oncogene, the latter by inactivating a tumor suppressor gene. Other unwanted sequelae may be induced by similar mechanisms (Wu et al., 1993).

Several practitioners in the art have made attempts to circumvent the undesirable consequences of random integration into the host chromosome. For example, they have exploited the idea of tethering the viral integrase protein to the site-specific DNA binding proteins. Such hybrid proteins should recognize specific DNA sequences on the chromosome and integrate the provirus specifically into those regions. However, it is not easy to map all the potential targets in the genome and the resulting hybrid proteins also have not been very efficient (Bushman, 1994; Goulaouic and Chow, 1996). Other strategies, though not entirely successful or simple, were proposed as well.

For example, U.S. Pat. No. 5,118,627 discloses a microbial shuttle vector independently replicative in bacterial and mammalian cells which includes in its DNA sequence bacterial plasmid sequences allowing replication in bacteria, and an SV40 viral ori and SV40 promoters and terminators.

U.S. Pat. No. 5,324,645 discloses a highly retrovirus producing DNA construct having a gene encoding retrovirus, which does not include a retrovirus long terminal repeat sequence. This construct is incorporated into a vector for gene amplification.

U.S. Pat. No. 5,338,674 discloses a live non-pathogenic RNA tumor virus having an altered genome that encodes the antigenic determinants of a pathogen but has no genes coding for pathogenicity.

U.S. Pat. No. 5,420,026 discloses self-assembled, replication defective, hybrid, and virus-like particles having capsid and membrane glycoproteins from at least two different virus types.

Facing the disadvantages associated with retroviral replication involving the obligatory integration step, the instant inventor came forward with a new invention that overcomes these drawbacks. In this application the inventor discloses the construction and testing of novel retroviruses and vectors derived from them that can replicate episomally in vertebrate cells without integration into the chromosomal DNA of the host, therefore rendering them safer for use in gene transfer, in gene therapy, and for vaccines.

GENERAL ASPECTS OF THE INVENTION

This invention is based on a surprising finding that a recombinant hybrid murine leukemia virus (MLV) can replicate in certain mouse cells without integration.

The infectious viral agent such as retrovirus is usually packaged as a virus particle or a virion. It consists of a capsid built of capsid proteins, virus-encoded enzymes, e.g., DNA polymerase, integrase, and protease, a viral RNA genome, which can carry a foreign nucleic acid of interest, and an envelope, in some cases comprising glycoproteins, spanning through the lipid membrane surrounding the particle. Following fusion of the virus envelope with the cellular membrane or endocytosis and virus release into the cytoplasm of the cell, the initial step in the replication involves a reverse transcription step. In this step the RNA genome, which in the case of retroviruses is flanked by short terminal repeats (termed R), is converted to a double-stranded linear DNA form, by virus-encoded reverse transcriptase (RT) or viral DNA polymerase. In this process of reverse transcription, the long terminal repeat (LTR) sequence is produced at each end of the double-stranded DNA. It is this two-LTR configuration that is integrated into the host cell genome by the virus-encoded integrase (IN). Integration occurs at random, or nearly random, sites on host chromosomal DNA. This integrated viral DNA is called a provirus.

Upon retroviral infection almost half of retroviral DNA (Cannon et al., 1996; Leavitt et al., 1996; Yang et al., 1980), goes through an abortive process whereupon the cellular ligase joins both viral ends forming one- or two-LTR circular molecules (Hong et al., 1991; Kulkosky et al., 1990; Pauza, 1990; Smith et al., 1990; Whitcomb and Hughes, 1991; Whitcomb et al., 1990). Under normal circumstances, both one-LTR and two-LTR molecules are rapidly lost from the cell and do not give rise to a new infectious viruses (Englund et al., 1995; Sakai et al., 1993; Stevenson et al., 1990). Thus, the prior art is unambiguous that retroviruses cannot replicate episomally or extrachromosomally unless they integrate into chromosomal DNA of a host cell.

However, this default in retroviral replication, as discovered by this inventor can be overridden. The solution to this problem is originally derived from a replication strategy of a small DNA virus.

One of the best-studied small DNA viruses is the simian virus 40 or SV40 (Shah, 1996). Other small DNA viruses replicate their DNA by a mechanism that closely resembles that of SV40 (Cole, 1996). One skilled in the art would recognize the similarity between the replication strategy described for SV40 and other similar small DNA viruses. For example, bovine papilloma virus or BPV uses so-called E1 and E2 proteins that are similar to analogous counterparts in SV40 (Piirsoo et al., 1996; Lehman and Botchan, 1998).

The instant invention discloses a polynucleotide construct encoding a recombinant retrovirus or vector that is capable, following the conversion of the viral RNA into DNA, of amplification and maintenance of the viral DNA as an extrachromosomal or episomal molecule. As used hereinafter the term episomal replication means that a virus such as retrovirus is able to replicate without integration into host's chromosomal DNA and without gradual loss from a dividing host cell also meaning that said virus replicates extrachromosomally or episomally. The retrovirus or vector is originally engineered to harbor the sequence coding for the origin of DNA replication or "ori" from a small DNA virus such as SV40. The term origin of DNA replication or ori as used herein means generally a regulatory genetic element found on an episomal DNA molecule allowing the replication of said DNA molecule so that these DNA molecules are not eventually lost upon division of a host cell. This mechanism assures stable extrachromosomal or episomal replication. Following infection, the double-stranded retroviral DNA is generated by means of reverse transcription and circularized upon entry into the host cell. The retrovirus carries ori and the host cell provides the cognate replication protein of small DNA virus, which is used for amplification and replication of the circular DNA retroviral genome. A replication protein can be so-called large T antigen of SV40 or it can be E1 or E2 of BPV. This is the first known hybrid retrovirus that does not have to integrate into the host genome in order to replicate efficiently in the host cells.

The instant invention also discloses a recombinant retrovirus or vector that is capable of amplification and maintenance of the viral DNA as an extrachromosomal molecule with the aid of minichromosome maintenance element (MME)—a regulatory element from bovine papilloma virus (BPV), which allows stable replication of episomal constructs without gradual loss from the host cell (Piirsoo et al., 1996).

Furthermore, the instant invention also discloses a recombinant retrovirus or vector that is capable of amplification and maintenance of the viral DNA as an extrachromosomal molecule without aid of ori and replication protein of the host cell. This is the first known hybrid retrovirus that does not integrate into the host genome in order to replicate efficiently in the host cells and does not use extraneous replication proteins.

The hybrid retroviruses described above are the first examples of a retrovirus that does not integrate into the host genome and therefore represents a novel and very important discovery that attains set forth goals of safety for medical purposes. Thus, the most important feature of this invention is the discovery that a recombinant retrovirus can efficiently replicate in host, e.g., human cells without integration. This feature is accomplished by using various recombinant strategies such as use of ori or MME and related elements, amphotrophic envelope, allowing stable episomal replication without loss from the host cell. Another important feature is a recombinant virus or vector replicating episomally without extraneous regulatory elements like ori or MME and replication proteins like large T antigen or E1 and E2.

SUMMARY OF THE INVENTION

The present invention provides a recombinant virus, viral vector, or transposon that has a novel replication strategy and which allows the creation of a virus that would replicate in vertebrate cells via reverse transcription without the danger of being "silenced" or of deregulating host genes upon integration into the host chromosome. The term transposon as used herein means a type of transposable element which, in addition to genes involved in transposition, carries other genes: often conferring selectable phenotypes such as antibiotic resistance or ability to replicate under unfavorable conditions. The term transposition as used herein means the movement of a fragment of nucleic acid around the template, usually through the function of transposable element. The term transposable element as used herein means a genetic element that has the ability to move (transpose) from one site on a template to another. The yeast Ty1 is a good example of LTR retrotransposon family.

In particular, the origin of DNA replication derived from a DNA virus is inserted into the genome of a virus that undergoes reverse transcription as a regular part of retroviral life cycle. After reverse transcription of the viral genomic RNA into DNA, the resulting molecule is circularized by cellular enzymes and, subsequently, replicates further as extrachromosomal DNA. Such extrachromosomal replication results in the amplification of this DNA intermediate in the cell, which, in turn, allows for viral replication and the production of either high titer viral stock or replication defective vectors. This process provides viruses and their respective vectors, which are quite safe for therapeutic purposes, such as gene transfer/therapy and other medical applications, such as viral or cancer vaccines. The said vaccines comprise both prophylactic vaccines and therapeutic vaccines.

Accordingly, it is a general object of the present invention to provide recombinant viruses, transposons and their vectors, which are capable, following the conversion of retroviral RNA into DNA, of amplification of same in the cell as episomes via DNA replication. The replication may be by any means except as a result of integration into the host chromosome, including, but not limited to, the presence of DNA sequences from DNA viruses, which define an ori or MME and encode a DNA replication protein. The replication may be by any means except as a result of integration into the host chromosome, without native DNA sequences from DNA, viruses, which define an ori or MME and encode a DNA replication protein such as T antigen or E1 and E2. The resultant recombinant viruses replicate without the necessity of integration into the host chromosome. The resulting virus can be infectious or non-infectious. The determination of that depends on viral myristilation of the gag protein, by differential splicing, by differential initiation of RNA transcription, and by the environment of the host cell or organism. The term non-infectious virus as used herein also means non-pathogenic virus, while infectious virus can be both pathogenic and non-pathogenic.

It is a further object of the present invention to provide an episomally replicating polynucleotide construct comprising retroviral sequences encoding at least one LTR of a retioviral genome, said retroviral sequences further comprising one or more mutations that disable the integration of said construct into host chromosomal DNA, said construct further having the capacity to replicate via reverse transcription, provided that any reverse transcription product obtained from such reverse transcription is also disabled from integrating into host chromosomal DNA.

It is a further object of the present invention to provide an recombinant temperate viruses, transposons and their vectors that are capable of infecting non-dividing cells.

It is a further object of the present invention to provide recombinant temperate viruses, transposons and their vectors that are capable of replicating in synchrony with host's replication cycle without causing cell lysis.

It is a further object of the present invention to provide recombinant viruses, transposons and their vectors that are capable of replicating via a "lytic" cycle, which would kill the host cell.

It is a further object of the present invention to provide recombinant viruses, transposons and their vectors that are capable of replication only in certain specific cells including but not limited to cells already infected with DNA virus which would provide necessary elements.

It is a further object of the present invention to provide a recombinant viruses, transposons and their vectors that are capable of replication only in certain specific cells, including but not limited to, tumor cells already infected with DNA virus, and capable of killing these cells in vitro and in vivo by means of, including but not limited to, run away replication, or by a toxic gene expression.

It is a further object of the present invention to provide a recombinant viruses, transposons and their vectors that have altered integrase protein or protein function and/or the cis elements necessary for integration or virtually any part of the genome that enhances the circularization of viral DNA and attenuates or abolishes integration.

It is a further object of the present invention to provide recombinant viruses, transposons and their vectors that have altered integrase protein or protein function but are able to replicate extrachromosomally and indefinitely without aid of SV40 T antigen or any extraneous native ori element or MME-like element from a small DNA virus.

It is a further object of the present invention to provide a recombinant viruses, transposons and their vectors which are either replication competent or defective that are capable of carrying a nucleic acid sequences of interest, infect host cells and express such a sequence in vertebrates or their cells in culture.

It is a further object of the present invention to provide a recombinant viruses, transposons and their vectors that are capable of carrying a nucleic acid sequences under the control of late promoters, such as SV40 late promoter or poxvirus late promoter, whose products are toxic to cells and may or may not alter or kill the cells.

It is a further object of the present invention to provide a recombinant viruses, transposons and their vectors that are capable of carrying a nucleic acid sequences devoid of the control of late promoters, such as SV40 late promoter or poxvirus late promoter, whose products are toxic to cells and may or may not alter or kill the cells.

It is a further object of the present invention to provide a recombinant viruses whose genomes are derived from but not limited to human immunodeficiency virus (HIV), Human T Lymphotropic Virus type I or II (HTLV), simian immunodeficiency virus (SIV), simian sarcoma virus (SSV), Rous sarcoma virus (RSV), caprine arthritis-encephalitis virus (CAEV), murine leukemia virus (MLV), avian leukemia virus (ALV), bovine leukemia virus (BLV), feline immunodeficiency virus (FIV), equine infectious anemia virus (EAIV), and endogenous retroviruses (ERV), including human endogenous retroviruses (HERV) which would use the replication strategy of this invention.

It is a further object of the present invention to provide host cells carrying the viruses, transposons and their vectors capable of expressing one or more nucleic acid sequences or genes and supporting the replication of such sequences or genes.

It is a further object of the present invention to provide tissue culture cells allowing generation of high titer virus stock by growing the cells transfected with the viral construct and allowing the virus to spread.

It is a further object of the present invention to provide a method for selection of viruses, transposons and their vectors for better replication including the use of marker gene transfer.

It is also an object of the present invention to provide methods for viruses, transposons and their vectors to transfer nucleic acid sequences into broad range of organisms or host cells of vertebrates, particularly humans both in vitro and in vivo.

It is also an object of the present invention to provide a means of generating transgenic animals.

It is a further object of the present invention to provide transgenic animals carrying the recombinant virus in at least one cell and capable of supporting the replication of thereof.

It is a further object of the present invention to provide methods for preventing and treating various diseases by gene transfer and vaccination and transfer of virus or vector harboring a nucleic acid sequence of interest to vertebrate hosts, preferably humans.

It is a further object of the present invention to provide methods for diagnostics of various diseases including but not limited to tumor cells or cells infected with other viruses.

These and other objects of the invention will become apparent by reference to certain examples, which are included herein for purpose of illustration and are not intended to be limiting.

BRIEF DESCRIPTION OF THE DRAWINGS

FIG. 1 illustrates a retroviral genome having an ori sequence derived from a DNA virus.

FIG. 3 illustrates retroviral replication that can occur without integration.

FIG. 6 illustrates nucleotide sequence of two CTR circle junctions as in Sequence ID Nos. 1–21.

DESCRIPTION OF THE PREFERRED EMBODIMENTS

Figure 2:
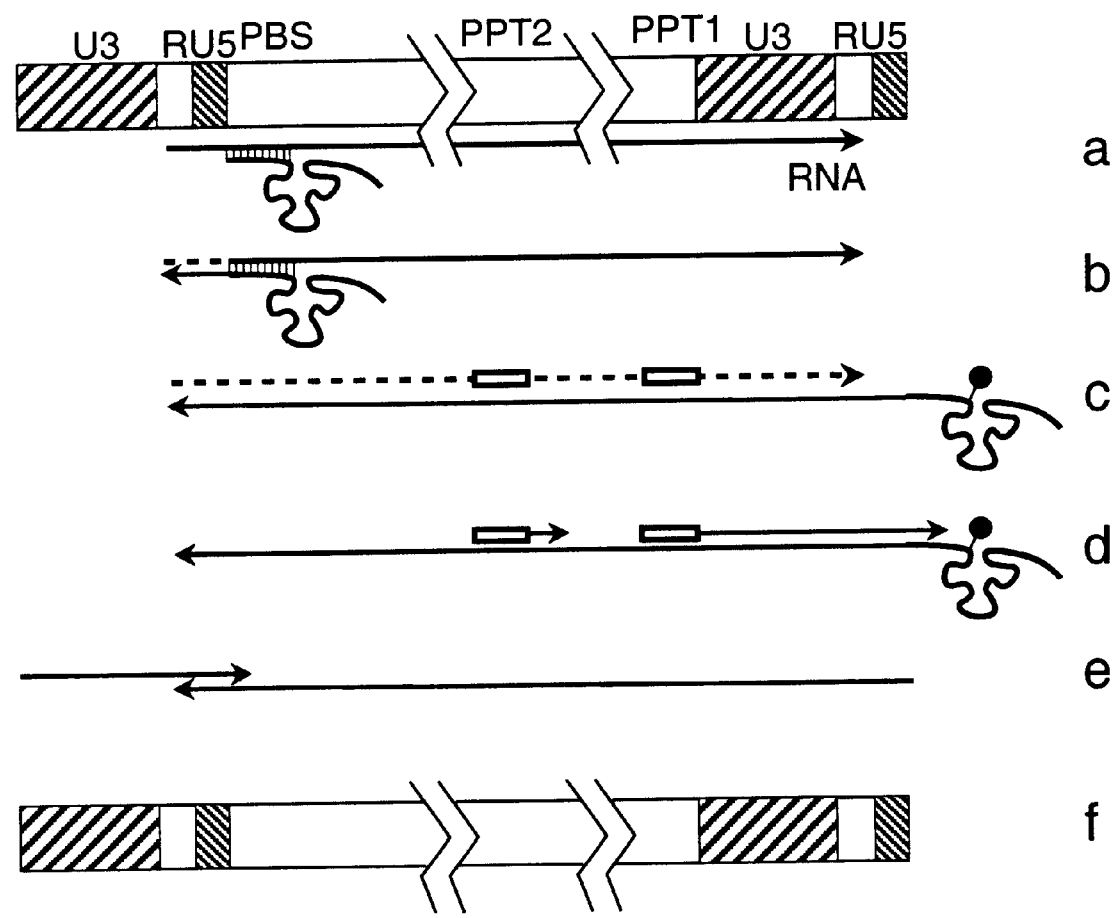
FIG. 2 illustrates an HIV having ori and large T antigen sequences derived from SV40.

Accordingly, the present invention is directed to a polynucleotide construct comprising retroviral sequences encoding at least one long terminal repeat (LTR) of a retroviral genome and can contain an ori, the retroviral sequences including one or more mutations that effectively disable the process of integration of viral DNA into host chromosomal DNA. Preferably, the polynucleotide construct is a ribonucleic acid construct and contains retroviral sequences encoding at least the 5' and 3' LTRs of a retroviral genome.

In one embodiment of the present invention, the polynucleotide construct permits the production of infectious virus particles from vertebrate cells that are transfected with the construct, the infective virus particles ultimately giving rise, in vertebrate cells infected therewith, to DNA molecules that are not integrated into host chromosomes but which are capable of extrachromosomal replication. That is, such DNA molecules are capable of replicating within the vertebrate cells infected with the infectious virus particles without integrating into the chromosomes of the cells. In still other embodiments, the polynucleotide construct is incapable either alone or in combination with helper constructs to produce infective virus particles.

The present invention contemplates polynucleotide constructs, including ribonucleic acid or deoxyribonucleic acid constructs, in which the retroviral sequences contained therein have been manipulated to disable the integration process. While this manipulation can be accomplished in a number of ways, a preferred way is the introduction of one or more mutations that involve an inverted repeat of at least one LTR. Alternatively, the one or more mutations may involve an integrase gene mutation and the like. In addition to the mutated sequences, the construct of the invention may further comprise other retroviral genes that encode a capsid, enzymes such as RT or DNA polymerase, enzymes as protease, e.g., aspartyl protease, viral envelope, auxiliary region, or combinations of such proteins.

When transfecting host cells, preferably vertebrate cells, with the polynucleotide constructs of the invention, host cells should preferably express a replication protein that supports the extrachromosomal replication of the DNA molecules that are ultimately produced from the reverse transcription process. Optionally, the genes encoding such replication support proteins can be introduced by the use of helper constructs. In certain embodiments such replication supporting protein is the large T antigen or E1 and E2 region of a DNA virus or any other DNA protein of the art capable of such function.

Furthermore, the polynucleotide constructs preferably further comprise a foreign gene (foreign to the retrovirus), such as a vertebrate gene, more preferably a mammalian gene, most preferably a human gene. For gene therapy applications, the foreign gene is preferably one that is either defective or absent from the host, or the host's cells, to which the polynucleotide constructs or resulting virus particles are administered.

In a particular embodiment of the present invention, the polynucleotide construct contains retroviral sequences from retroviral genomes selected from, though not limited to, HIV, HTLV, MLV, AMV, ALV, BLV, SSV, RSV, CAEV, SIV, HERV, ERV, EAIV, or FIV. The ori, on the other hand, may be selected from one that is found in a DNA virus. Generally, the DNA virus may be selected, for example, from papova viruses or herpes viruses. Examples of papova viruses include, but are not limited to SV40, human or bovine papilloma virus (HPV or BPV), polyoma virus (Py), and human SV40-like viruses (Dorries et al., 1994; Elsner and Dorries, 1992) such as BK (BKV) or JC (JCV). Examples of herpes viruses include, but are not limited to herpes simplex virus (HSV), cytomegalovirus (CMV), Epstein-Barr virus (EBV), varicella or chickenpox virus, herpes zoster or shingles virus.

Thus, in a particular aspect of the invention, a polynucleotide construct is provided which comprises retroviral sequences encoding all the genetic elements necessary for the production of an infectious virus particle, including the 5' and 3' long terminal repeats (LTRs) of a retroviral genome, and an ori or MME, the retroviral sequences including one or more mutations that effectively disable the process of integration of viral DNA into host chromosomal DNA. Any DNA molecules arising from a reverse transcription process involving RNA of the infectious virus particle are able to replicate within host vertebrate cells without integrating into the chromosomes of the cells.

In a particular aspect of the invention, a polynucleotide construct is provided which comprises retroviral sequences encoding essentially all genetic elements necessary for the production of an infectious virus particle, including the 5' and 3' long terminal repeats (LTRs) of a retroviral genome and the retroviral sequences including one or more mutations that effectively disable the process of integration of viral DNA into host chromosomal DNA, but without ori or MME sequences which function as normal T antigen or E1 and/or E2 counterparts. Furthermore in this situation the host cell is a normal cell without exogenous large T antigen or DNA virus' antigen serving the function of T antigen. DNA molecules arising from a reverse transcription process involving RNA of the infectious virus particle are able to replicate indefinitely within host vertebrate cells without integrating into the chromosomes of the cells.

The present invention also contemplates a vaccine comprising retroviral sequences encoding all the genetic elements necessary for the production of an immunogenic virus particle, including the 5' and 3' long terminal repeats (LTRs) of a retroviral genome, and an ori or MME, the retroviral sequences including one or more mutations that effectively disable the process of integration of viral DNA into host chromosomal DNA.

On inoculation of a subject, the vaccine of the present invention provides still more immunogenic virus particles that can stimulate but not overwhelm an immune system of the subject, e.g., vertebrate host such as mammal, preferably a human Especially contemplated are vaccines that are based on a retrovirus, including but not limited to ERV, MLV, AMV, ALV, BLV, SSV, RSV, CAEV, HIV, HTLV, SIV, EAIV, or FIV.

Unlike prior recombinant vaccines, the vaccines of the present invention have the capacity to establish a latent infection in a vertebrate host.

Still other aspects of the present invention relate to cancer vaccines comprising retroviral sequences encoding all the genetic elements necessary for the production of an infectious virus particle, including the 5' and 3' long terminal repeats (LTRs) of a retroviral genome, and an ori or MME, the retroviral sequences including one or more mutations that effectively disable the process of integration of viral DNA into host chromosomal DNA, such that any DNA molecules arising from a reverse transcription process involving RNA of the infectious virus particle are able to replicate within selected cells of vertebrate host, without integrating into the chromosomes of the cells. Ideally, the cancer vaccine is administered to a host whose cells express one or more tumor markers on the cell surface.

In a particular embodiment, the cancer vaccine comprises nucleotide sequences encoding a cytokine capable of stimulating the action of an immune system of the vertebrate host. Cytokines useful for this purpose are well known in the art and for example one can find a general description of them in Davis et al., (Current progress in the gene therapy of cancer. Curr Opin Oncol 1996 November; 8(6):499–508).

In still other embodiments, the cancer vaccine includes a gene encoding a chemokine. The chemokines are a complex superfamily of small, secreted proteins that were initially characterized through their chemotactic effects on a variety of leucocytes. The superfamily is divided into families based on structural and genetic considerations and have been termed the CXC, CC, C and CX3C families. Chemokines from these families have a key role in the recruitment and function of T lymphocytes. Moreover, T lymphocytes have also been identified as a source of a number of chemokines. T lymphocytes also express most of the known CXC and CC chemokine receptors to an extent that depends on their state of activation/differentiation and/or the activating stimuli. For example, two chemokines CXCR4 and CCR5, together with the regulated production of their respective ligands, appears to be extremely important in HIV infection. The intracellular events which mediate the effects of chemokines, particularly those elicited by the CC chemokine RANTES, include activation of both G-protein- and protein tyrosine kinase-coupled signaling pathways.

It should be apparent to those of ordinary skill that a variety of tumor markers may be expressed on the surface of affected cells. Such one or more tumor markers may be selected from the group consisting of a tumor marker for a suppressor gene mutation or the presence of an oncogene. For example, the suppressor gene can be p53, p73, p51, p40, or one homologous to ket rat gene (see for review K. Novak, All in p53 family. Nature Medicine Vol. 4, p 771, 1998). For example, the oncogene can be c-myc, c-jun, c-fos, c-rel, c-qin, c-neu, c-src, c-abl, c-lck, c-mil/raf, c-ras, c-sis, and c-fps.

In another embodiment the gene therapy approach can be also based on enzyme/pro-drug systems such as HSVtk/ganciclovir or CD/5-fluorocytosine which involves the transfer of suicide genes that convert inactive pro-drugs into cytotoxic compounds. Examples of such approaches are known in the art can be found for example in the U.S. Pat. No. 5,691,177.

The present invention further contemplates a polynucleotide construct comprising retroviral sequences encoding at least one long terminal repeat (LTR) of a retroviral genome and an origin of DNA replication, the retroviral sequences including one or more mutations that effectively disable the process of integration of viral DNA into host chromosomal DNA, the polynucleotide construct alone, on introduction into a host vertebrate cell, being incapable of producing infective virus particles. In particular, the polynucleotide construct of the present invention, upon introduction into a host vertebrate cell, along with one or more helper constructs containing retroviral genes encoding viral proteins, permits the production of virus particles that are either infectious or non-infective depending on the nature or identity of the retroviral sequences contained in the construct and the retroviral genes contained in the one or more helper constructs.

In yet another aspect of the invention, a nucleic acid is contemplated which comprises retroviral sequences and origin of DNA replication or their equivalents, in which the retrovirus is replication deficient. Preferably, the retrovirus is replication deficient and contains an additional foreign gene. Furthermore, the present invention contemplates a viral particle that comprises such a nucleic acid.

In yet another aspect of the invention, a nucleic acid is contemplated which comprises retroviral sequences with genetically altered T antigen responding origin of DNA replication sequences or their equivalents, in which the retrovirus is replication deficient. Preferably, the retrovirus is replication deficient and contains an additional foreign gene. Furthermore, the present invention contemplates a viral particle that comprises such a nucleic acid.

The nucleic acids of the present invention are useful in a variety of applications including the introduction of one ore more nucleic acid sequences into a host cell, subject, or patient, who may benefit from the expression product of the nucleic acid sequence. The nucleic acid can be introduced by conventional means or via a virus particle comprising same. On introduction of the nucleic acid, virus particle, or other vehicle the expression product of same has the potential for preventing, diagnosing, or treating a particular condition in the cell, subject, or human patient.

Of particular interest is the production of transgenic animals via the nucleic acid constructs, viral particles, or other vehicles of gene introduction of the present invention. Preferably, the animal host chosen as the recipient of the foreign gene, preferably a human gene, can support replication of the virus of the present invention. More preferably, the animal host can support replication of the virus only in certain specific cells.

Other methods, which are apparent to those of ordinary skill in the art, having considered the disclosure provided herein, include a method of providing gene therapy to an individual comprising the introduction of a desired nucleic acid sequence into a host cell or an individual. The introduction is most conveniently effected by infecting a host cell or individual with a viral particle according to the present invention.

Still other methods may include a method of providing diagnostics for the presence of tumor cells or cells infected with a DNA virus in an individual, which method comprises infecting a host cell in vitro or an individual in vivo with a viral particle of the invention and observing any changes in the phenotype or genotype of the cell or individual consistent with the presence of the tumor cells or cells infected with a DNA virus.

In order that the invention herein described may be more fully understood, the following detailed description is set forth. This invention relates to recombinant viruses and their vectors capable of transferring nucleic acid sequences into broad range of host cells and animals and replicate by a novel mechanism. In general, as shown in FIG. 1, the genome of recombinant viruses and vectors of this invention comprise of a capsid region, enzyme region, including but not limited to pol region of retroviruses (encoding protease, reverse transcriptase and integrase), an env region or surface region, and an origin of DNA replication and a replication supporting protein which can use such origin, or the functional equivalents of thereof. More specifically, as shown in FIG. 3, the recombinant virus comprises but is not limited to at least one LTR, gag, pol, env and other genes of human immunodeficiency virus type (HIV) and ori and large T antigen of simian virus 40 (SV40). The ori and large T antigen sequences of SV40 can be replaced (but is not limited) by the equivalents from BK virus (BKV), JC virus (JCV), herpes simplex virus (HSV) or papillomavirus like HPV or BPV. The recombinant viruses are capable of carrying the nucleic acids sequences of interest, infect and replicate efficiently in broad range of cells and animals without the necessity of integrating into the host genome. The viruses of this invention also can be replication defective.

Gag, Pol, and Env in FIG. 1 are retroviral genes, which encode the structural proteins that form the viral particle. The gag, pol, and env regions of the virus can be derived from any retrovirus including but not limited to HIV, SIV and MLV. These regions can encode for all or only parts of the gag, pol, and env genes. It also can be a chimera between different proteins, although for a replication competent virus it is preferable that the sequence encodes for the fully functional protein. By the way of example the HIV-1 gag, pol, and env regions are used.

LTR in FIG. 1 facilitates the retroviral replication and contains promoters and enhancers for transcription of the viral genome. The LTR derived from any retrovirus may be used but it is not limited to retroviral LTR. For replication competent virus the functional LTR is preferably used. By the way of example the HIV-1 LTR region is used.

The packaging signal is a region on the RNA, which encodes signal for RNA packaging into the viral particles. The appropriate viral packaging signal may be used. Other genes and elements including but not limited to Rev, RRE, Tat, Vif, Nef, capsid, protease, polymerase, surface or env proteins and gene X may be used in viruses of this invention.

Origin of DNA replication (ori) in FIG. 1, is a sequence allowing double-stranded DNA to be replicated. It is usually recognized by the replication-associated proteins like large T antigen. The ori elements including but not limited to papovaviruses may be used. By the way of example the SV40 ori is used.

The major early viral replication protein, like large T antigen in FIG. 2, or E1 and E2 proteins are proteins which recognize the ori or MME and together with the host enzymes, initiate DNA replication. The large T antigen of papovaviruses may be used, although viral replication proteins from DNA viruses like, but not limited to, papilloma or other than papovaviruses also may be used. By the way of example the SV40 large T antigen is used. One skilled in the art will also recognize that virtually any nucleotide sequences of any virus or transposon but without any native ori and any replication protein from virtually any genome may be used. Conventional methodology including but not limited to molecular biology techniques known to those skilled in the art can be used to generate viruses of this invention.

In one embodiment the recombinant viruses, transposons and their vectors use a novel strategy of replication amplifying the DNA intermediate as extrachromosomal DNA. Foreign genes derived from any source, whose expression in the host is desired, are incorporated into the viral genome and are designated as Q. These genes may be used for preventive therapeutic purposes, as markers, vaccines or for other functions.

In another embodiment, the MLV is used to generate the recombinant retrovirus of the invention and the ori of polyomavirus may be inserted. In a preferred embodiment, the foreign nucleic acids of interest are inserted downstream the env gene. The polyoma large T antigen may be provided in trans.

Another aspect of the present invention is to provide viruses, transposons or a vector, which is capable of replication via lytic cycle.

Another aspect of the present invention is to provide viruses, transposons or a vector, which is capable of replication via non-lytic cycle.

Another aspect of the present invention is to provide a viruses, transposons and their vectors which are capable of replication in only certain cells in the host which include but are not limited to cancer cells causally linked to another virus such as SV40 and papilloma virus.

Another aspect of the present invention is to provide a transgenic animal in which only certain cells can support replication of the virus of this invention and can be altered or destroyed by thereby. These animals may be used but are not limited to study of disease and evaluation of therapies and vaccination.

Another aspect of the present invention is to provide a method for altering the retroviral integrase protein or function or the inverted repeat (IR) found on the tips of linear retroviral DNA intermediate, or virtually an part of viral genome to enhance the circularization of viral DNA molecule and to attenuate or abolish the integration process. This may include, but is not limited to RT and RNAse H.

Another aspect of the present invention is to provide a method for altering the retroviral and retrotransposon reverse transcription process to enhance the formation of the circular DNA molecules.

Another aspect of the present invention is to provide a method for using the recombinant vectors to transfer one or more nucleic acids sequences of interest to a broad range of host species and their cells, which may include but is not limited to use of amphotropic envelope or envelopes of other viruses like but not limited to vesicular stomatitis virus G (VSV-G). Once inside the cell, the recombinant virus (vector) make a DNA copy of viral genome which is circularized and stably replicated as episome and can be expressed in the host cell.

Another aspect of the present invention is to provide a method for using a useful property of the retrovirus or retroviral vector; the ability to replicate in the easily maintained cells e.g. tissue culture cells allowing generation of high titer virus stock by growing the cells transfected with the viral construct and allowing the virus to spread.

The recombinant virus of the invention may be directly introduced into host cells or may be inserted into a plasmid or other construct, which is then inserted into a host cell. For example the viruses of the invention may be cloned into a plasmid for propagation of DNA in appropriate cell. Example of the cell that might be used include but are not limited to *Escherichia coli*. It will be also understood to those skilled in the art that the plasmid carrying the recombinant virus DNA should contain additional elements necessary for transfer and subsequent replication and selection of the construct in the host system.

Another aspect of this invention is to provide host cell in which the recombinant virus or vector containing all or part of the nucleic acid sequences of interest can be propagated. The host cells containing the recombinant virus of this invention include but are not limited to vertebrates such as mice, monkey and humans. The host cells may be used to produce viruses or viral vector stocks.

In another aspect of this invention the recombinant viruses or vectors of this invention may be used to transfer nucleic acid of interest for therapeutic purposes in humans or in other mammals in need of gene therapy. The viruses may be administered to animal or individual in need of such therapy in a variety of ways. Viruses from host cells which release the virus into supernatant fluid may be administered by administering the supernatant fluid or the host cells. The purified form of the virus or vector can be administered to the vertebrate in need of treatment alone or in the form of a pharmaceutical composition.

Gene therapy may be also accomplished by inserting the foreign nucleic acid sequences of interest into the virus or vector of the invention and then introducing the virus or vector into the cell or organism. The infected host cell will express the desired therapeutic agent. The cells expressing the agent may be administered or implanted in the organism or individual in need of therapy.

The host cells may be from virtually any species. In one embodiment the host cells are taken from the individual in need of therapy. Examples of such cells include, but are not limited to stem cells, hematopoietic stem cells and T cells. In another embodiment the cells are from a different individual or different species.

Means of administering the host cells containing the recombinant virus or vector of the invention include but are not limited to, intravenous, intramuscular, intralesional, subcutaneous or intraperitoneal injection or implantation. Alternatively the cells containing the virus may be administered locally by topical application, direct injection into an affected area or by implantation of a porous device containing cells from the host or another species which contain and express the virus or vector or the protein of interest.

Examples of diseases that might be suitable for gene therapy include but are not limited to viral diseases, neurological disorders, coronary or heart problems, and/or cancer.

In yet another aspect of the invention, the recombinant virus or vector can be used to generate transgenic animal carrying the virus in at least one cell. It may be introduced into an animal at an embryonic stage. Examples of the animals into which the virus can be introduced include, but are not limited to non-human primates, dogs, cats, cows, sheep, horses, mice, rats or other rodents. Such animals may be used, but are not limited to use as biological models for study of diseases, evaluation of diagnostic or therapeutic methods for disease or vaccines or to generate a vaccine.

The recombinant virus or vector of this invention may be used to generate transgenic animals with or without additional foreign nucleic acid sequences.

It is further aspect of the invention to use the recombinant viruses or vectors to deliver a prophylactic or therapeutic vaccine for a wide variety of vertebrates and particularly for human diseases. Thus, the term vaccine as used herein means both prophylactic or preventive modality as well as therapeutic modality. A prophylactic immunization is provided in advance of any evidence of the disease and serves to prevent or attenuate the disease. When provided therapeutically, the vaccine is provided at or after diagnosis or onset of the disease to enhance the immune response of the patient or animal to the disease of interest and to treat or attenuate the disease. The vaccine, which acts as an immunogen, may be administered in virtually any form and into virtually any cell known to those skilled in the art. The pure form or substantially pure form of the virus or vector can be administered to the vertebrates in need of treatment alone or in the form of a pharmaceutical composition.

It is further aspect of the invention to use the recombinant viruses or vectors to deliver the vaccines as a cancer vaccines which include, but are not limited to transfer of the virus or vector to the tumor cells ex vivo and then after irradiating them, administering back to the individual.

If the individual is already afflicted with the disease the therapeutic vaccine can be administered in conjunction with other therapeutic treatments.

One skilled in the art will know the parameters to determine the correct titer of particles to be administered. The therapy may be administered as often as necessary. The preventive and therapeutic methods described herein may be used alone or in conjunction with additional therapy known to those skilled in the art for the treatment of a given disease or condition.

EXAMPLES

Example 1

General Procedure

The inventor designed and constructed several viruses that are hybrids between a retrovirus and a small DNA virus. These hybrids use a different replication strategy in their life cycle. These viruses serve for the design of new vaccines against different viruses, including HIV, as well as for cancer vaccines and vectors for gene therapy.

First step in construction of the hybrid retroviruses is to introduce, by PCR, unique SfuI restriction site into Moloney murine leukemia virus on the plasmid pNCA (Colicelli and Goff, 1985) just downstream of the envelope open reading frame. The mouse polyoma (Py) virus ori sequence is amplified by PCR on the plasmid template pHG20 (Gassmann et al., 1995) creating DNA fragment flanked by SfuI sites (FIG. 1). This fragment is introduced into the SfuI sites of the modified viral DNA. The retroviral integrase gene is mutated by introduction of the HindIII-SalI DNA fragment from plasmid S247 IN-, which contains the integrase coding region with the EcoRI linker insertion rendering the integrase protein inactive and viral replication deficient (Lobel and Goff, 1984; Roth et al., 1990). Another mutation is introduced, by PCR, into the inverted repeat (IR), which is found on the tip of the 3U LTR of the preintegrative linear viral DNA (see FIG. 2). This sequence, recognized by integrase, is required for viral replication (Murphy et al., 1993; Murphy and Goff, 1992; Reicin et al., 1995). The resulting plasmid is then purified, verified by restriction analysis, sequenced, and finally transfected into MOP-8 cells (ATCC #CRL-1709) (Muller et al., 1984). This mouse cell line stably expresses the polyoma large T antigen, the only protein required for successful polyoma replication or maintenance of the plasmid harboring the Py ori (Gassmann et al., 1995). After transfection, viral growth is monitored by measuring the endogenous RT activity in the medium. The presence of the polyoma ori sequences is also monitored by PCR amplification of the viral cDNA followed by agarose gel electrophoresis.

The virus stock is used to infect fresh MOP-8 cells. The cell-free virus is usually passaged three times. Throughout these passages, it maintained the ori sequences, the linker inserted into the integrase region, and the IR mutation. Even one of the mutations introduced into the virus, either the one in retroviral integrase or the one in IR, inhibits integration and viral replication (Murphy et al., 1993; Murphy and Goff, 1992; Roth et al., 1990). Integration of the retrovirus harboring the ori sequence into chromosome of the cell expressing the large T antigen is an event leading to cell death (Cole, 1996). Therefore, the maintenance of the ori in the virus and both introduced mutations, in integrase and in IR, would suggest that the virus replicates without integration and uses the extrachromosomal DNA as its replication intermediate in the infected cell.

The experiments are carried out in three steps:

1) Construction of the hybrid virus
2) Cell transfection and testing
3) Virus passage, viral growth kinetics, and its characterization.

1) MLV derivative with the SV40 ori and with amphotropic envelope is constructed. The construction of this hybrid virus requires reagents that are readily available and are used in prior constructs. The origin of DNA replication from SV40 (nucleotide position on SV40 genome 5171-133) is amplified by PCR from the plasmid template pSV2NEO (Southern and Berg, 1982), and at the same time SfuI sites flanking the ori is introduced using oligonucleotide VLSI 5'-CCCCCTTCGAAGCTTTTTGCAAAAGCCTAGGCC-3' (SEQ ID NO 21) and VLS2 5'-CCCCCTTCGAAGCAT GCATCTCAATTAGTCAGC-3' (SEQ ID NO 22). This DNA fragment is cut with SfuI, gel purified and cloned into the unique SfuI site of the plasmid pVIT550 this plasmid harbors the mutations in the IR sequence and integrase gene (see FIG. 2). The DNA fragment SalI-ClaI, containing MLV amphotropic envelope 10A 1, from plasmid pRR151 (Ott et al., 1990), is introduced into the plasmid containing MLV and the SV40 ori. The linker insertion mutation in the integrase coding region is introduced by replacing the fragment Sal I-SalI from the mutant virus with the corresponding fragment from the plasmid S247 IN–(Roth et al., 1990).

A plasmid with a control virus is also constructed; this plasmid harbors the same sequences as the previously described one with the exception that the SV40 ori is cloned into the vector sequences and outside the viral sequences. For this purpose, the SV40 ori is amplified and the EcoRI site is introduced into the amplified DNA by PCR using oligonucleotide VLS3 5'-CCCCGAATTCAAGCTTTT TGCAAAAGCCTAGGCC-3' (SEQ ID NO 23) and VLS4 5'-CCCCGAATTCGCATGCATCTCAATFAGTCAGC-3' (SEQ ID NO 24). The resulting EcoRI fragment is cloned into the EcoRI site, which is upstream the retroviral sequence. This plasmid DNA replicates in the cells after transfection, just like the previously described plasmid, but does not give rise to any infectious viruses because the ori sequence is not maintained within the virus. The previously constructed MLV containing the Py ori, mutation in integrase, and IR is used as another control. Finally, a similar virus with no ori is used as another control virus as well. All plasmids containing these control viruses do not give rise to infectious particles, because the viruses they encode are integration-defective and cannot replicate via an extrachromosomal DNA intermediate. Alternatively, retroviruses comprising HIV or SIV with the SV40 ori are constructed and used as in above disclosed manipulations.

2) The 293T cells, which stably express SV40 large T antigen (Pear et al., 1993), are transfected with plasmid DNA containing the modified viruses by the calcium phosphate method. Appearance of virus in the medium is monitored, at different time points, by standard reverse transcriptase assay of the cell-free culture medium (Telesnitsky et al., 1995).

Alternatively, transfected cells are co-cultivated with COS7 cells (Gluzman, 1981). These are monkey cells that stably express SV40 large T antigen and support replication of plasmids carrying the SV40 ori. Such plasmids replicate to very high copy numbers and to levels that far exceed those of the same plasmids in human cells expressing SV40 large T antigen (Chittenden et al., 1991). Therefore, the COS7 cells are producing more of virus. Another way to produce the hybrid retroviruses is to transfect the plasmid DNA into Jurkat/T-ag, H9/T-ag and CEM/T-ag. These are human CD4+ T-cell lines that stably express SV40 large T antigen, and are used as alternative means for virus production. These cells are also co-cultivated with the COS7 cells to increase viral production.

As a control, the 293 cells (Graham et al., 1977) (parental cell line of the 293T that does not express T antigen) are transfected with the constructed plasmids. Although these cells transiently produce the virus they do not replicate the plasmid DNA or support productive viral infection. As another control, both cell lines (293 and 293T) are transfected with the panel of control viruses described earlier (with SV40 or Py ori, with ori outside the viral sequences or without ori). All the control viruses are replication deficient in both cell lines. When T-cell lines are used then their respective parental cell lines serve as appropriate control cells.

Transfected cells are harvested at one day intervals, and the small cellular DNA is extracted by Hirt method and subjected to DNA blot analysis using DNA probes spanning the MLV sequence and also SV40 ori sequence. The donor plasmid DNA is about 11 kb long. After the virus initiates infection, the DNA blot from later time points accumulates faster migrating DNA band of about 8 kb, representing the two-LTR circular viral DNA. This circular molecule is shorter because it is missing the plasmid vector sequences, which are lost during retrovirus replication (see FIG. 3). In the alternative approach, the single-LTR and double-LTR circular DNA viral molecules are analyzed by restriction digest with enzymes whose recognition sites flank the LTR region, followed by Southern blot analyses (Wiskerchen and Muesing, 1995).

3) The viruses produced after transfection are used to infect fresh cells. The hybrid retroviruses might require adaptation for the new replication life style. The genome of retroviruses mutates at relatively high frequency. This high mutation rate is mainly due to the reverse transcription step, which is known to be an error prone process (Katz and Skalka, 1990). These hybrid viruses would be expected to go through a selection process in which the faster replicating viruses would overgrow the initial viral population (Barsov and Hughes, 1996). Most genetic changes would be expected to occur in the integrase coding region, inverted repeat, and perhaps also reverse transcriptase.

The approximate multiplicity of infection (MOI) for the initial experiments is between 0.1 and 0.5. This relatively high MOI is used initially so as to assure that there are enough cells infected with viruses in the culture to give rise to infectious virions. The MOI is then slowly decreased at every passage to allow for progressively more stringent selection for the faster replicating viruses. To monitor this selection process, the cell supernatant samples are collected at different times during virus growth in subsequent viral passages, and the viral growth kinetics are compared using the RT assay. Fresh 293T cells are infected with the supernatant from previous viral infection. This procedure is repeated three to four times. The viral kinetics is then compared with that of wild-type MLV.

The viruses replicating in the 293T cells are tested for several characteristics. DNA blot analysis is used to monitor the formation of the two LTR circular molecules and comparing their abundance with that of linear viral DNA. This experiment allows to test possibility that viral integrase would adapt to enhance the formation of the two LTR circles to allow for better virus replication. The maintenance of the integrase linker insertion in subsequent passages is monitored by restriction analysis followed by DNA blot analysis. Alternatively, to test for the linker insertion, the viral cDNA is amplified by PCR, then cut with restriction enzymes, and analyzed by agarose gel electrophoresis (Lauermann and Boeke, 1997). The maintenance or any changes in the inverted repeat sequence is also monitored. The viral DNA spanning the LTR-LTR junction region are amplified by PCR using the appropriate primers and directly sequenced by fluorescent dideoxy IBI sequencing method. Alternatively, the PCR product is first cloned into the plasmid, by using the AT cloning kit, and then several plasmids are sequenced. The average copy number of the extrachromosomal retroviral circular DNA in the 293T cells is determined and compared with the number in the COS7 cells. For this, the total DNA is extracted from the cells and analyzed by DNA blot analysis. Two DNA probes are used: one from the viral sequence spanning the LTR-LTR junction, representing the circular viral DNA, and one that hybridizes to a single copy cellular sequence like actin gene. As a control, cells infected with wild-type MLV, which integrates prevalently as a single copy into the genome, are used. The intensity of detected bands on the blot is quantified by IBI Phospho Imager. After the DNA probes have been standardized for their relative intensity, the ratio of a single cellular gene signal compared with the signal obtained from the viral DNA represents an average copy number of the circular viral DNA in the cell culture population.

Example 2

Non-integrating HIV Replicating Via DNA Episome

In order to investigate directly the ability of a lentivirus to replicate without integration into the host genome the HIV-1 LAI virus harboring the SV40 ori in place of part of nef gene upstream the polypurine tract (PPT) is constructed. The system where the major early replication protein, large T antigen form SV40 is provided in trans is developed. In this system human T cell lines CEM, H9 and Jurkat are transfected with construct expressing large T antigen and further selected for stable expression of thereof. The cells are maintained in RPMI 1640 medium supplemented with 10% fetal bovine serum, penicillin and streptomycin. The human cells 293 are transfected with the nucleic acid of the above viral construct. The 293 produced virus is used to infect the CEM, H9 and Jurkat cells stably expressing T-antigen and the viral growth is monitored by in vitro reverse transcriptase (RT) assay.

Example 3

Non-integrating HIV Self Replicating Via DNA Episome

The HIV-1 LAI virus harboring SV40 ori and large T-antigen upstream the 3U LTR and a partial nef deletion is constructed. The virus contains the integrase protein in which the critical amino acid residues in the catalytic domain are mutated rendering it integration defective. The virus is able to infect susceptible cells. Followed reverse transcription and circularization of its cDNA the viral nucleic acid is maintained in the cell as extrachromosomal DNA. This DNA is a template for newly synthesized viral RNA, which after synthesis of viral proteins gives rise to a new infectious virions or virus particles.

Example 4

Non-integrating Moloney Murine Leukemia Virus (MoMLV) Replicating Via DNA Episome In order to investigate directly the ability of a mouse virus to replicate without integration into the host genome the MoMLV harboring the polyoma replication ori sequence downstream of the env gene and upstream the PPT inserted into the BstBI site which is introduced by PCR is constructed. The cell line where the major early replication protein, large T antigen from mouse polyoma virus is provided in trans is used. The nucleic acid of MoMLV described above is transfected into the MOP-8 cell line expressing polyoma large T antigen by electroporation and the resulting viral growth is monitored.

Example 5

Infection and Specific Killing of Cells Expressing Major Early SV40 Protein

The MoMLV harboring the SV40 ori sequence downstream of the env gene and upstream the PPT inserted into the BstBI site described in example 3 is constructed. After transfection into producer cells NIH 3T3 the resulting virus from the supernatant is used to infect monkey COS7 cells (those cells stably express the SV40 large T antigen), which are engineered to stably express the MoMLV receptor protein. Hence rendering them susceptible to the infection by MoMLV virus particles. The cell death is monitored visually under the microscope every day. The amount of DNA episome containing the MoMLV sequence in the cell culture is monitored by Southern blot analysis using the MoMLV sequence as a probe.

Example 6

Cancer Vaccine or Infection and Immunization of Mice With Non-integrating MoMLV Replicating Via DNA Episome The MoMLV harboring the polyoma virus ori described above is used to infect transgenic mice expressing the polyoma virus large T antigen. The mice is then challenged with wild-type MoMLV virus, which causes leukemia in about 8 month after inoculation. The mice immunized with the non-integrating virus are protected against the challenge with the wild-type virus. Yet another way of providing gene therapy is to introduce into a host with a tumor expressing mutated suppressor cancer gene such as p53 a recombinant virus of the instant invention carrying functional p53, which would then express and suppress the tumorigenic process.

Example 7

Gene Therapy or Specific Killing of Only Cells Expressing the Papillomavirus and Method of Making Packaging Cells The MVL replication defective vector containing a papillomavirus ori and a toxic gene, under the control of a papillomavirus promoter, is used to transfect the packaging cell line containing the amphotropic helper virus. Methods of how obtaining such packaging cells lines are well known in the art and one can use an approach as disclosed in the U.S. Pat. No. 5,766,945. This helper virus has altered integrase protein so it cannot integrate the vector sequences into the recipient cell chromosome. The resulting viral stock is used to locally infect the patient with a cervical cancer caused by the papillomavirus. The vector infects randomly cancer cells and neighboring normal cells. However, it can only replicate in the cancer cells, which can support, after circularization, the DNA replication of the vector. The toxic gene is expressed and specifically kills only the tumor cells. The examples of toxic genes are found for example in U.S. Pat. Nos. 5,691,177 or 5,652,130.

Example 8

Diagnosis of Human Tumor Cells Transformed by Papillomavirus

The MVL vector containing papillomavirus ori, of a specific human papillomavirus type, and the marker gene, under the control of a papillomavirus promoter, is used to transfect the packaging cell line containing the amphotropic helper virus. The resulting virus is used to infect the cervical patient material in vitro. If the tested cells are positive for the specific type of the papillomavirus this will support the replication of thereof and the expressed marker gene will allow for the visual diagnosis of the tested cells. Thus, one skilled in the art, can identify papilloma virus-caused squamous carcinoma cells in a cervical biopsy of a patient suspected to have such a tumor. For this purpose the biopsy sample cells are infected with a polynucleotide construct containing an ori which is dependent on DNA replication protein of papilloma virus expressed by carcinoma cells. The polynucleotide construct may further comprise a marker enzyme such as peroxidase. Upon addition of peroxidase substrate onto cells of interest those that express the enzyme will identified as carcinoma cells.

Example 9

Transgenic Animal Expressing Episomally Replicating Polynucleotide Construct

Many cancers and immune disorders afflicting humans are associated with retroviral expression. The real reason and mechanism of these phenomena is not well known. A transgenic animal model helps to find optimal treatment and prevention modalities in humans and other animals. Transgenic mouse is produced herein by transferring the construct of interest into embryonic stem cell, or fertilized oocyte, which is then reimplanted into female foster-mother recipient according to standard methods, e.g., method disclosed in U.S. Pat. No. 4,396,601. As a result of a such experimentation, a few mice are born, carrying and expressing the gene of interest in all tissues. The tissues, i.e., fibroblasts, from these mice are also useful as they grow in tissue culture and thus provide an in vitro model as well. Thus, such a transgenic mouse is also a source of cell lines expressing episomal construct. Other transgenic animals, e.g., rats, rabbits as well as insects can be made according to standard procedures well known to those skilled in the art. Transgenic plants, e.g., potato, tobacco, banana, etc., can also be made according to standard procedures well known to those skilled in the art.

Example 10

The Growth Kinetics of Viruses at Different Passages

Figure 4:
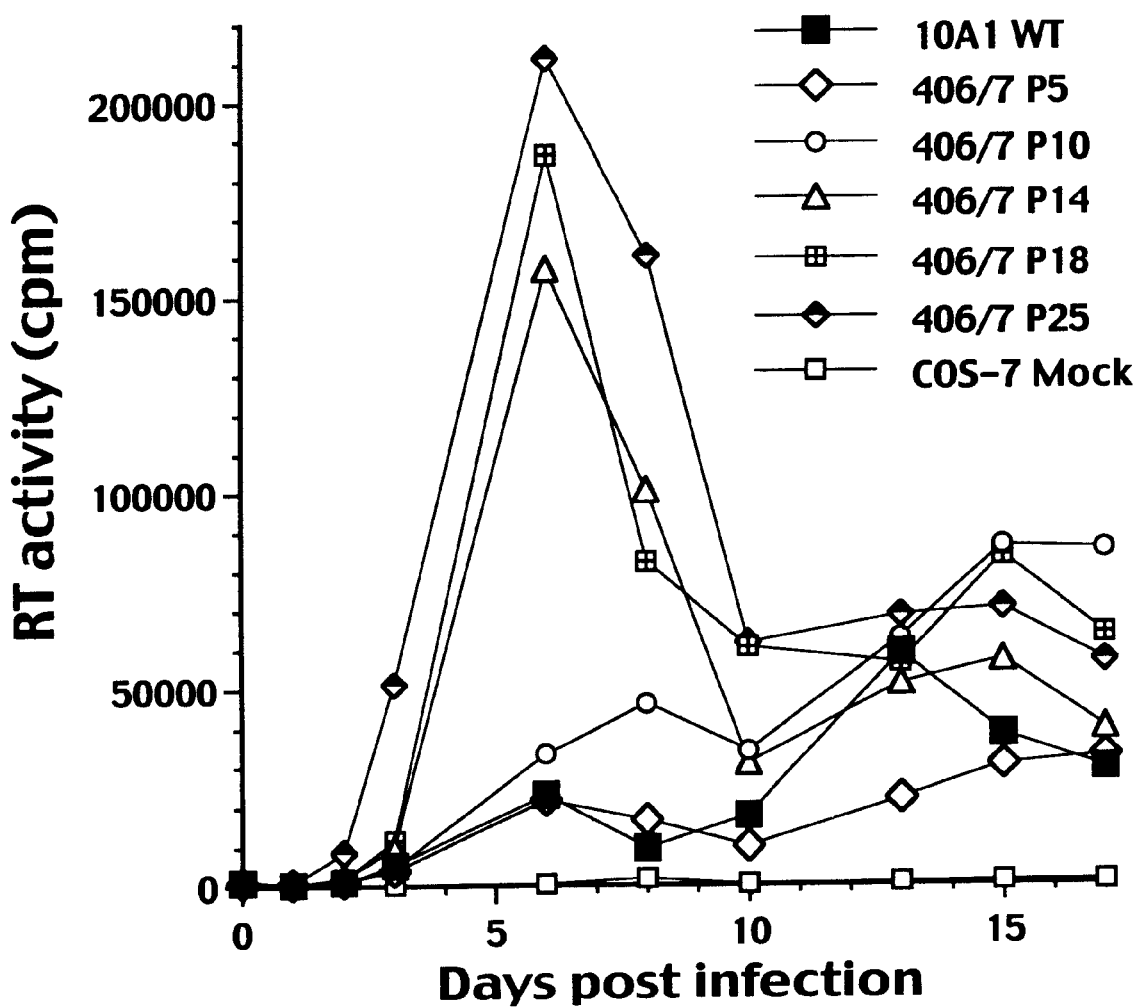
FIG. 4 illustrates growth kinetics of viruses at different passages.

The amphotropic MLV containing SV40 ori, pVIT406, as well as wild-type amphotropic MLV(10A1) are propagated on COS7 cells. The viral supernatants from individual passages are collected and stored at −80° C. Following passage 24 viral supernatants from all passages are used to infect COS7 cells, to eliminate possible effect of storage on virus viability. After 12 days the cell culture supernatants are assayed for RT activity and cell free medium containing equal amount of RT activity (approximately equivalent to multiplicity of infection (MOI) 0.01) is used to infect fresh COS7 cells. Cell culture medium is collected at time point indicated and assayed at the end of the experiment. Cells are generally split 1:6 every 5–7 days. RT assay is performed as described elsewhere. 10A1–wild-type amphotropic MLV; P5–passage 5; 406–pVIT406 (amphotropic MLV with SV40 origin, disabled integrase and mutated inverted repeat in the LTR) (FIG. 4).

Example 11

The Growth Kinetics of Viruses With Opposite Orientation of the SV40 Origin

Figure 5:
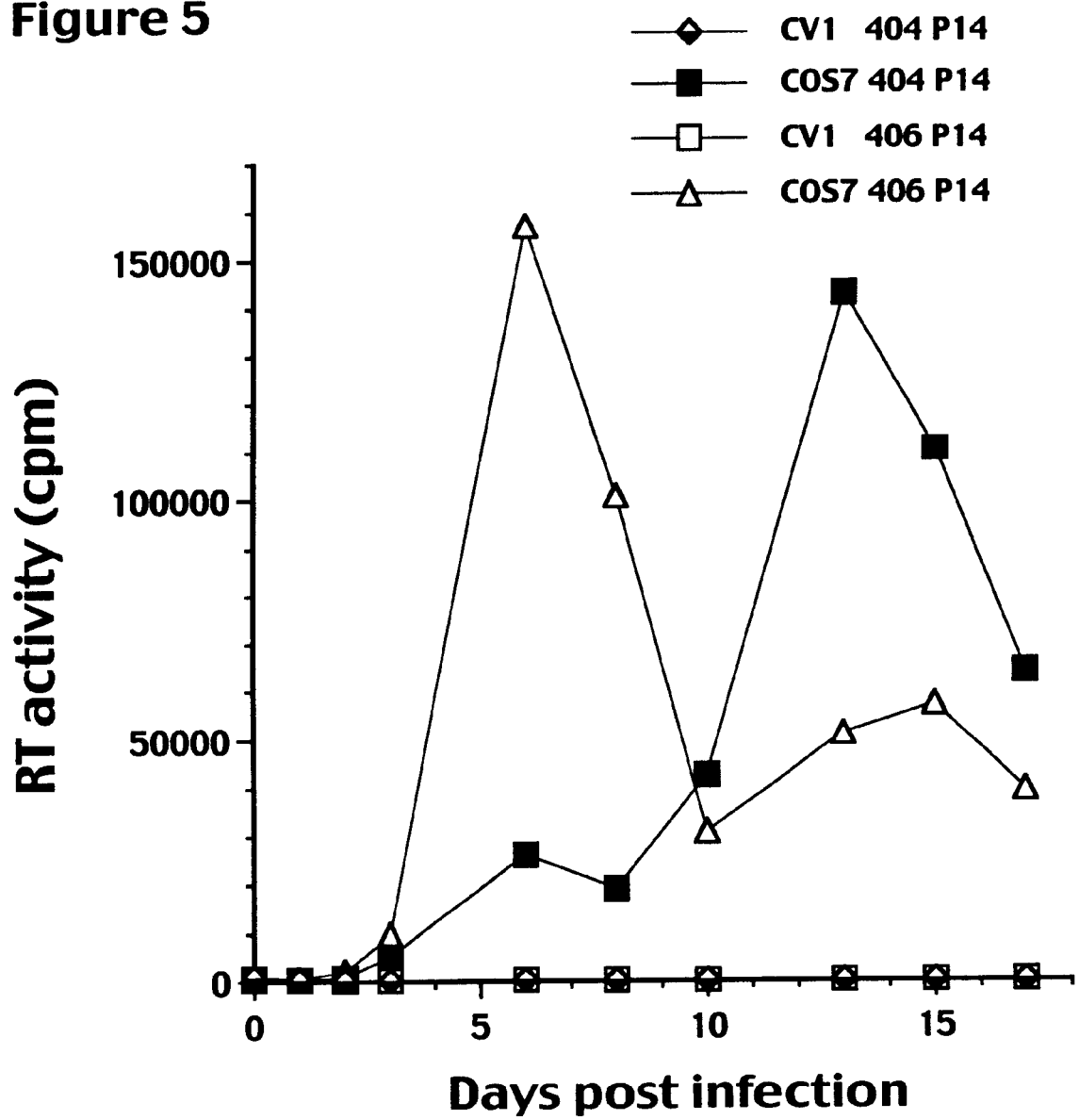
FIG. 5 illustrates growth kinetics of viruses with opposite orientation of the SV40 origin.

Kinetics of virus replication is compared by infecting COS7 cells. CV1 cells served as negative control for virus replication. The experimental setup is as in Example 10. 404–pVIT404 virus with SV40 origin in orientation such as the late transcription (large T-ag induced) is in opposite orientation than the retroviral one; 406—same virus as above except the SV40 origin is in opposite orientation i.e. the SV40 origin late transcription is same as the retroviral one; P14–passage 14. The virus 404 has consistently slower growth kinetics in all passages. The kinetics of viruses with opposite origin orientation at passage 14 is shown (FIG. 5).

Example 12

Nucleotide Sequence of Two LTR Circle Junctions

DNA from cells infected with ori-containing MLV is prepared as described elsewhere. The PCR products are separated on agarose gel, purified and coned into plasmid using 5 Prime-3 Prime PCR Cloner Cloning Kit. The resulting plasmids are analyzed and clones with appropriate size inserts sequenced using IBI fluorescent automated system. Nucleotides representing the ends of viral DNA are aligned. Extra nucleotides between two LTR, of unknown origin, are shown and separated from the ends of linear DNA by gaps. The nucleotides, which mutated from the starting viral clone sequence are underlined. WT–wild type MLV; SMC–MLV molecular clone used for initial infection; 1–2 pVIT404 passage 20; 3–11 pVIT406 passage 20; 12–19 pVIT406 passage 21;U5, U3 opposite ends of 3U and 5U LTR respectively. The terminal nucleotides which are removed by integrase prior integration and nucleotides mutated in the starting viral molecular clones are shown in FIG. 6. FIG. 6 illustrates nucleotide sequence of two CTR circle junctions as listed in Sequence ID Nos. 1–21.

Example 13

Figure 7:
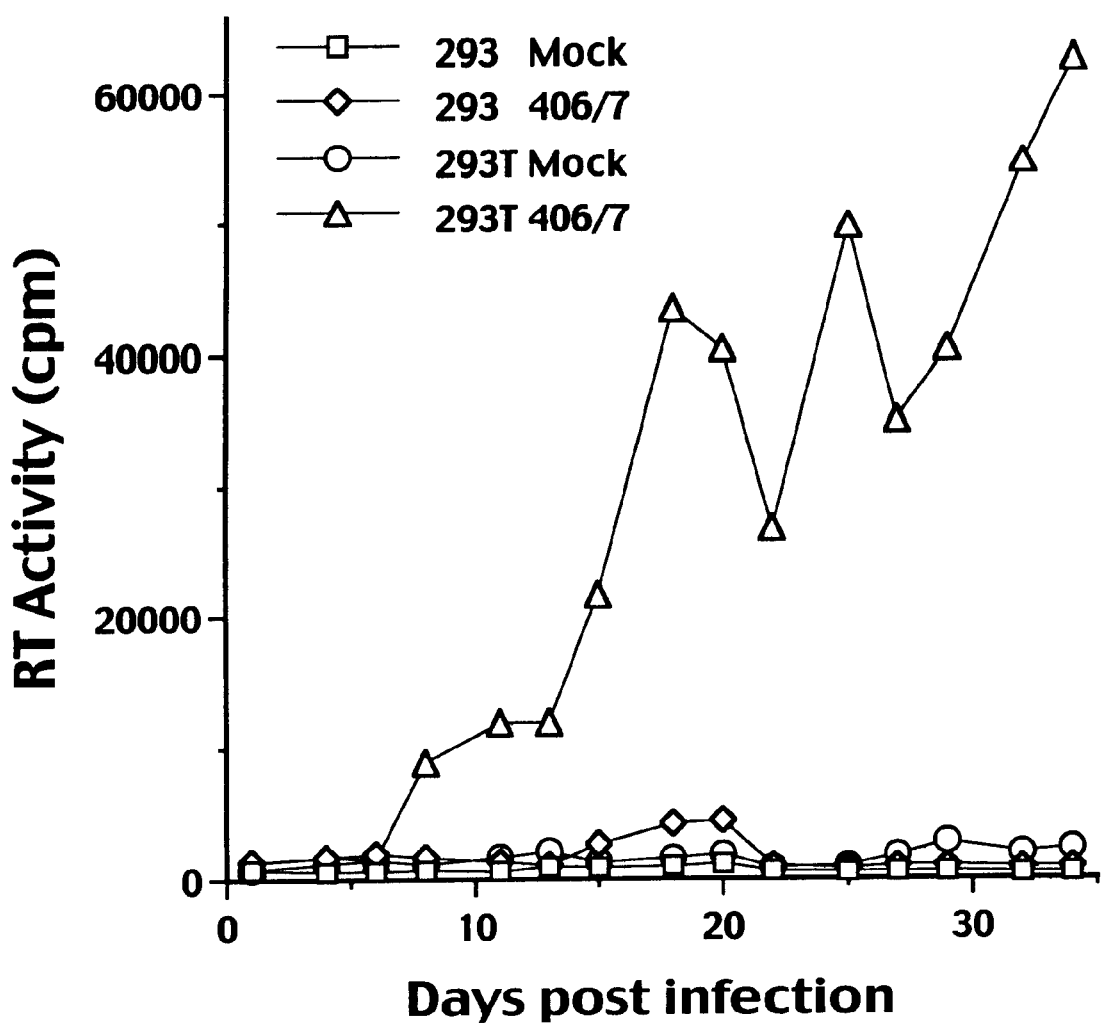
FIG. 7 illustrates that 293T and 293 cells can support replication of the SV40 containing MLV.

293T and 293 Cells Can Support Replication of the SV40 Containing MLV 293 cells are infected as negative control experiment for the hybrid viral replication. These cells are transiently infected but would neither support productive infection nor produce any particles that could be passaged on fresh 293 cells. These cells are monitored for infection by DNA blot analysis, which allows one to follow the maintenance or disappearance of the retroviral DNA. After extensive passage of these infected 293 cells, the integrated viral DNA is examined by DNA blot analysis. This integrated DNA is usually not present. The positive control for this experiment is the wild-type amphotropic MLV, which infects human cells with relatively high efficiency and integrates into their genome. 293 and 293T cells are infected with pVIT406 viral supernatant from passage 20 or mock infected as control. 293 cells devoid of T antigen can support the replication of new retroviral constructs (see small peaks around day 20). Viruses from these peaks are collected and analyzed by PCR. When standard RT assay is not sensitive enough to detect the RT activity of the viruses produced into the medium, the PCR-based RT (PBRT) assay, a very sensitive test that is developed to detect very low amounts of reverse transcriptase activity in the medium, is used (Maduru and Peden, 1997). The results reveal that despite apparent lack of replication by a standard RT analysis more sensitive PCR analysis indicates genuine viral replication. Experimental design as in Example 10 and results are shown in FIG. 7.

Example 14

293T Cells can be Re-infected Using Virus Rroduced by 293T Cells

Figure 8:
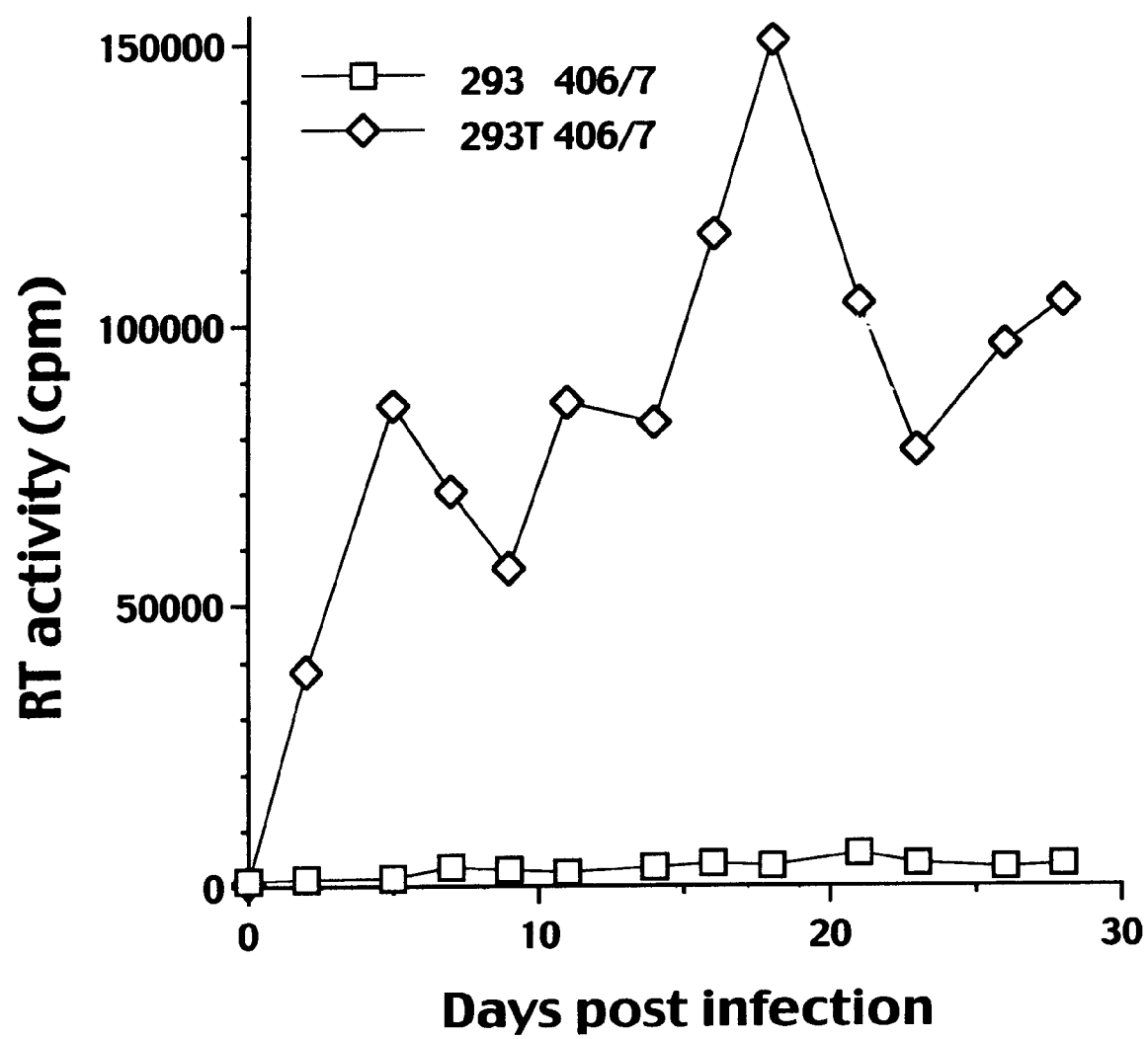
FIG. 8 illustrates that 293T cells can be re-infected using virus produced by 293T cells.

Cell free virus from time point at day 18 (from FIG. 4) from 293 is used to infect fresh 293 and from 293T is used to infect fresh 293T cells at relatively high MOI of 0.1. It appears that only virus from culture supernatants from 293T cells (293T 406/7) give rise to productive infection of fresh cells. However, more sensitive analysis by the PCR-based RT (PBRT) assay, a very sensitive test that is developed to detect very low amounts of reverse transcriptase activity in the medium (Maduru and Peden, 1997) reveals that some of the virus (293 406/7) can replicate episomally even in T antigen devoid 293 cells (FIG. 8).

Example 15

Wild-type Amphotropic MLV but not pVIT406 Productively Infects CV1 Cells

Figure 9:
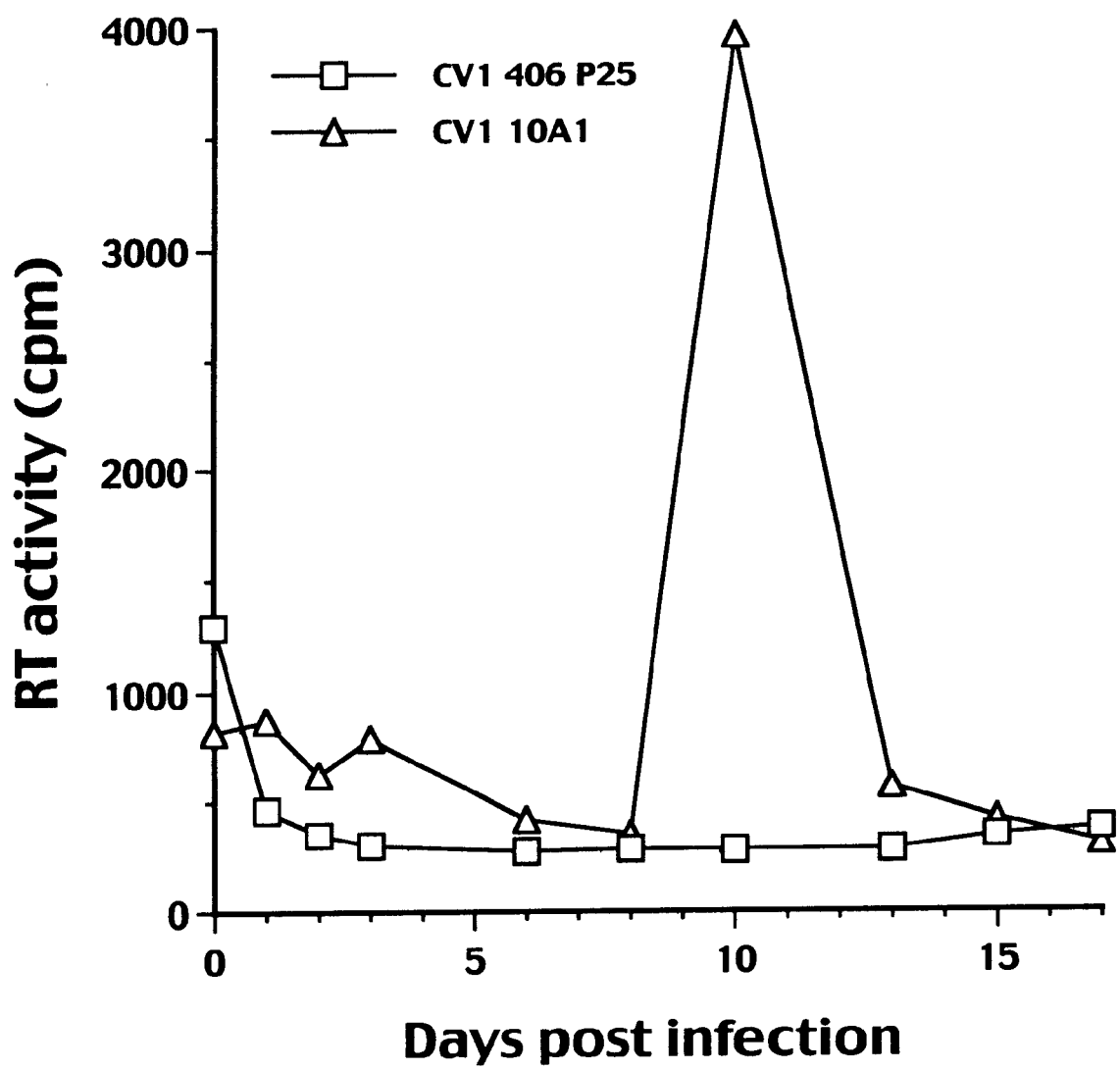
FIG. 9 illustrates that wild-type amphotropic MLV but not pVIT406 productively infects CV1 cells.

CV1 cells do not contain SV40 large T antigen. It is a parental cell line for COS7 line. CV1 cells are infected with pVIT406 from passage 25 or with wild-type amphotropic MLV(10A1) at MOI 0.1. Only 10A1 virus is able to establish productive infection. 10A1 retroviral env protein is commonly used to make amphotropic retroviruses and for detailed description of the methodology one can consult U.S. Pat. No. 5,766,945. Experimental design as in Example 10 and results are shown in FIG. 9.

Example 16

The Sequence of Viral Integrase Demonstrates That New Constructs are not Capable to Integrate Into the Host Genome The viral DNA is extracted from COS7 cells infected with pVIT406 virus, passage 20. The integrase sequence is PCR amplified using multiple sets of primer pairs spanning the integrase gene and directly sequences using IBI fluorescent automated sequencing system. The integrase gene after 20 passages contains multiple conservative and non-conservative amino acid changes. It also possesses the EcoRI linker insertion.

Example 17

Regulatory Elements Other Than SV40 Elements Provide Stable Episomal Replication Regulatory elements allowing stable episomal replication such as E1 and E2 and MME from BPV are described by others (Piirsoo et al., 1996) and they support the principle that for example HIV-1 LAI virus constructs harboring and/or responding to such elements can replicate in hosts cells such as human cells lacking SV40 regulatory elements. In this system human 293 cell line expressing E1 and E2 is transfected with a construct additionally containing upstream regulatory region (URR) including E2-dependent transcriptional enhancer or minimal origin of replication (MO) and a part of open reading frame (ORF) or alternatively with MME only which is found within URR with or without MO. Some of these constructs replicate with efficiency similar to constructs dependent on SV40-containing and/or responding elements. The stable episomal replication is tested by a serial passaging method as described in above examples. It is thus evident that previously described constructs lacking SV40 elements are able replicate in host cells due to a mechanism that is similar in principle to MME-dependent replication maintenance machinery which means that additional, previously unrecognized episomal replication-controlling elements do exist.

It will be apparent to those skilled in the art that the examples and embodiments described herein are by way of illustration and not limitation, and that other examples may be used without departing from the spirit and scope of the present invention, as set forth in the appended claims.

What is claimed is:

1. A polynucleotide construct comprising retroviral sequence encoding at least one LTR, polypurine tract and packaging signal of a retroviral genome of an episomally replicating retrovirus, which is able to replicate without requirement of integration, said retroviral sequences further comprising one or more mutations that disable the integration of said construct into host chromosomal DNA, said construct further having the capacity to replicate via reverse transcription, provided that any reverse transcription product obtained from such reverse transcription is also disabled from integrating into host chromosomal DNA, said retroviral sequence further comprising a heterologous sequence encoding a gene product of interest.

2. The polynucleotide construct of claim 1 in which said retroviral sequence further comprise the 5' and 3' LTRs.

3. The polynucicotide construct of claim 1 in which said retroviral genome is selected from the group consisting of HIV, HTLV, MLV, AMV, ALV, BLV, SSV, RSV, CAEV, SIV, ERV, EAIV and FIV.

4. The polynucleotide construct of claim 1 in which said retroviral sequence further comprise an origin of DNA replication.

5. The polynucleotide construct of claim 4 in which said origin of DNA replication is one found in a DNA virus.

6. The polynucleotide construct of claim 5 in which said DNA virus is selected from the group consisting of papova viruses or herpes viruses.

7. The polynucleotide construct of claim 1 in which said one or more mutations are within an inverted repeat of a LTR or an integrase.

8. The polynucleotide construct of claim 1 which further comprise a capsid, polymerase, protease, integrase, envelope, auxiliary region, or combination of same.

9. The polynucleotide construct of claim 1 in which said heterologous sequence is a foreign gene.

10. The polynucleotide construct of claim 1 in which said heterologous sequence is a vertebrate gene.

11. The polynucleotide construct of claim 9 in which said foreign gene is either defective or absent from a host cell.

12. The polynucleotide construct of claim 1 in combination with retroviral genes carried by one or more helper constructs, wherein said combination encodes integration defective infectious virions.

13. A composition comprising retroviral sequence encoding all the genetic elements necessary for the production of an immunogenic virion, including one or more LTRs, said genetic elements including one or more mutations that disable the integration of viral DNA into host chromosomal DNA, such that any DNA molecules arising from a reverse transcription step involving an RNA of said immunogenic virion are able to exist episomally within host vertebrate cells, said virion further being able to replicate without requirement of integration, said retroviral sequence further comprising a heterologous sequence encoding a gene product of interest.

14. The retroviral sequence of claim 13 in which said episomal existence provides an immunogenic virion that can stimulate an immune system of a vertebrate host.

15. The retroviral sequence of claim 13 in which said immunogenic virion is a retrovirus.

16. The composition of claim 15 in which said retrovirus is selected from the group consisting of MLV, AMV, ALV, BLV, SSV, RSV, CAEV, HIV, HTLV, SIV, ERV, EAIV, or FIV.

17. The composition of claim 13 which used in cancer cells.

18. The retroviral sequence of claim 13 which is able to exist episomally within selected cells of a vertebrate host.

19. The heterologous sequence of claim 13 which comprises nucleotide sequences encoding a cytokine or chemokine.

20. The heterologous sequence of claim 13 which comprises a gene encoding a protein that converts a pro-drug into a cytotoxic agent.

21. The heterologous sequence of claim 13 which comprises one or more tumor markers expressed in selected cells of a host into which said composition has been introduced.

22. The heterologous sequence of claim 21 which said one or more tumor markers are selected from the group consisting of a suppressor gene or an oncogene.

23. The heterologous sequence of claim 22 in which said suppressor gene is selected from a group consisting of p53, p73, p51, p40, or ket gene.

24. The heterologous sequence of claim 22 in which said oncogene is selected from a group consisting of c-myc, c-jun, c-fos, c-rel, c-qin, c-neu, c-src, c-abl, c-lck, c-mil/raf, c-ras, c-sis, or c-fps.

* * * * *

SEQUENCE LISTING

```
<160> NUMBER OF SEQ ID NOS:  22

<210> SEQ ID NO 1
<211> LENGTH: 69
<212> TYPE: DNA
<213> ORGANISM: Murine leukemia virus

<400> SEQUENCE: 1
tgactacccg tcagcggggg tctttcatta atgaaagacc ccacctgtag gtttggcaag      60
ctagcttaa                                                             69

<210> SEQ ID NO 2
<211> LENGTH: 70
<212> TYPE: DNA
<213> ORGANISM: Murine leukemia virus

<400> SEQUENCE: 2
tgactacccg tcagcggggg tctttcatta atgtatgtcg cgacctgtag gtttggcaag      60
gctagcttaa                                                            70

<210> SEQ ID NO 3
<211> LENGTH: 76
<212> TYPE: DNA
<213> ORGANISM: Murine leukemia virus

<400> SEQUENCE: 3
tgactacccg tcagcggggg tctttcatac ctccaaatgt atgtcacgac ctgtaagttt      60
```

```
ggcaaggcta gcttaa                                                  76

<210> SEQ ID NO 4
<211> LENGTH: 80
<212> TYPE: DNA
<213> ORGANISM: Murine leukemia virus

<400> SEQUENCE: 4
tgactacccg tcagcggggg tctttcattg tatgtcgcaa atgtatgtcg cgacctgtag   60
gtttggcaag gctagcttaa                                              80

<210> SEQ ID NO 5
<211> LENGTH: 76
<212> TYPE: DNA
<213> ORGANISM: Murine leukemia virus

<400> SEQUENCE: 5
tgactacccg tcagcggggg tctttcatac ctccaaatgt atgtcacgac ctgtaggttt   60
ggcaaggcta gcttaa                                                  76

<210> SEQ ID NO 6
<211> LENGTH: 69
<212> TYPE: DNA
<213> ORGANISM: Murine leukemia virus

<400> SEQUENCE: 6
tgactacccg tcagcggggg tctttcatta tgtatgtcac gacctgtacg tttggtaagg   60
ctaggttaa                                                          69

<210> SEQ ID NO 7
<211> LENGTH: 72
<212> TYPE: DNA
<213> ORGANISM: Murine leukemia virus

<400> SEQUENCE: 7
tgactacccg tcagcggggg tctttcattg gaatgtatgt cgcgacctgt aggtttggca   60
aggctagctt aa                                                      72

<210> SEQ ID NO 8
<211> LENGTH: 70
<212> TYPE: DNA
<213> ORGANISM: Murine leukemia virus

<400> SEQUENCE: 8
tgactacccg tcagcggggg tctttcattaa tgtatgtcgc gacctgtagg tttggcaagg   61
ctaacttaa                                                          70

<210> SEQ ID NO 9
<211> LENGTH: 70
<212> TYPE: DNA
<213> ORGANISM: Murine leukemia virus

<400> SEQUENCE: 9
tgactacccg tcagcggggg tctttcatta atgtatgtcg cgacctgtag gtttggcaag   60
gctagcttaa                                                         70

<210> SEQ ID NO 10
<211> LENGTH: 61
<212> TYPE: DNA
```

<213> ORGANISM: Murine leukemia virus

<400> SEQUENCE: 10
tgactacccg tcagcggggg tctttcattc gcgacctgta ggtttggcaa ggctagctta     60
a                                                                     61

<210> SEQ ID NO 11
<211> LENGTH: 73
<212> TYPE: DNA
<213> ORGANISM: Murine leukemia virus

<400> SEQUENCE: 11
tgactacccg tcagcggggg tctttcattt ttaatgtatg tcgcgacctg taggtttggc     60
aaggctagct taa                                                        73

<210> SEQ ID NO 12
<211> LENGTH: 74
<212> TYPE: DNA
<213> ORGANISM: Murine leukemia virus

<400> SEQUENCE: 12
tgactacccg tcagcggggg tctttcattc gagaatgtat gtcgcgacct gtaggtttgg     60
caaggctagc ttaa                                                       74

<210> SEQ ID NO 13
<211> LENGTH: 70
<212> TYPE: DNA
<213> ORGANISM: Murine leukemia virus

<400> SEQUENCE: 13
tgactacccg tcagcggggg tctttcatta atgtatgtcg cgacctgtag gtttggcaag     60
gctagcttaa                                                            70

<210> SEQ ID NO 14
<211> LENGTH: 69
<212> TYPE: DNA
<213> ORGANISM: Murine leukemia virus

<400> SEQUENCE: 14
tgactacccg tcagcggggg tctttcatta tgtatgtcgc gacctgtagg tttggcaagg     60
ctagcttaa                                                             69

<210> SEQ ID NO 15
<211> LENGTH: 70
<212> TYPE: DNA
<213> ORGANISM: Murine leukemia virus

<400> SEQUENCE: 15
tgactacccg tcagcggggg tctttcatta atgtatgtcg cgacctgtag gtttggcaag     60
gctagcttaa                                                            70

<210> SEQ ID NO 16
<211> LENGTH: 74
<212> TYPE: DNA
<213> ORGANISM: Murine leukemia virus

<400> SEQUENCE: 16
tgactacccg tcagcggggg tctttcatta cccaatgtat gtcgcgacct gtaggtttgg     60
caaggctagc ttaa                                                       74

```
<210> SEQ ID NO 17
<211> LENGTH: 74
<212> TYPE: DNA
<213> ORGANISM: Murine leukemia virus

<400> SEQUENCE: 17
tgactacccg tcagcggggg tctttcatta ccaaatgtat gtcgcgacct gtaggtttgg      60
caaggctagc ttaa                                                       74

<210> SEQ ID NO 18
<211> LENGTH: 68
<212> TYPE: DNA
<213> ORGANISM: Murine leukemia virus

<400> SEQUENCE: 18
tgactacccg tcagcggggg tctttcattt ggatgtcgcg acctgtaggt ttggcaaggc      60
tagcttaa                                                              68

<210> SEQ ID NO 19
<211> LENGTH: 70
<212> TYPE: DNA
<213> ORGANISM: Murine leukemia virus

<400> SEQUENCE: 19
tgactacccg tcagcggggg tctttcatta atgtatgtcg cgacctgtag gtttggcaag      60
gctagcttaa                                                            70

<210> SEQ ID NO 20
<211> LENGTH: 69
<212> TYPE: DNA
<213> ORGANISM: Murine leukemia virus

<400> SEQUENCE: 20
tgactacccg tcagcggggg tctttcaaaa tgtatgtccc gaccggtagg tttggcaagg      60
ctaacttaa                                                             69

<210> SEQ ID NO 21
<211> LENGTH: 72
<212> TYPE: DNA
<213> ORGANISM: Murine leukemia virus

<400> SEQUENCE: 21
tgactacccg tcagcggggg tctttcattc taatgtatgt cgcgacctgt aggtttggca      60
aggctagctt aa                                                         72

<210> SEQ ID NO 22
<211> LENGTH: 74
<212> TYPE: DNA
<213> ORGANISM: Murine leukemia virus
<220> FEATURE:
<221> NAME/KEY: LTR
<222> LOCATION: 32..58
<223> OTHER INFORMATION: Letter "n" represents nucleic acid bases A or
      C or G or T/U or unknown

<400> SEQUENCE: 22
tgactacccg tcagcggggg tctttcatta anatntgtnt ctancnannn gtnggnnngg      60
gaaagctaac ttaa                                                       74
```